(12) United States Patent
Tabuteau

(10) Patent No.: US 10,137,131 B2
(45) Date of Patent: *Nov. 27, 2018

(54) PHARMACEUTICAL COMPOSITIONS COMPRISING MELOXICAM

(71) Applicant: AXSOME THERAPEUTICS, INC., New York, NY (US)

(72) Inventor: Herriot Tabuteau, New York, NY (US)

(73) Assignee: AXSOME THERAPEUTICS, INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/936,176

(22) Filed: Mar. 26, 2018

(65) Prior Publication Data

US 2018/0214380 A1   Aug. 2, 2018

Related U.S. Application Data

(63) Continuation-in-part of application No. PCT/US2018/012433, filed on Jan. 4, 2018.
(Continued)

(51) Int. Cl.
*A61K 9/20* (2006.01)
*A61K 31/4196* (2006.01)
(Continued)

(52) U.S. Cl.
CPC ........ *A61K 31/5415* (2013.01); *A61K 9/0053* (2013.01); *A61K 9/205* (2013.01); *A61K 9/2009* (2013.01); *A61K 9/2086* (2013.01); *A61K 31/4196* (2013.01); *A61K 47/6951* (2017.08); *A61P 29/00* (2018.01)

(58) Field of Classification Search
CPC ............ A61K 31/4196; A61K 31/5415; A61K 9/2009; A61K 9/205; A61P 29/00
See application file for complete search history.

(56) References Cited

U.S. PATENT DOCUMENTS 5,284,269 A   2/1994 Petrie et al.
5,835,407 A   11/1998 Lee
(Continued)

FOREIGN PATENT DOCUMENTS

CA   2565941 A1   11/2005
CN   101987081      3/2011
(Continued)

OTHER PUBLICATIONS

Hu et al., Predicting Biological Functions of Compounds Based on Chemical-Chemical Interactions, PLoS One, 6(12), Dec. 2011, 9 pgs.
(Continued)

*Primary Examiner* — Savitha M Rao
(74) *Attorney, Agent, or Firm* — Maschoff Brennan; Brent A. Johnson; Yuefen Zhou

(57) ABSTRACT

Disclosed herein are compositions comprising a drug such as a triptan (e.g. rizatriptan) and/or an NSAID (e.g. meloxicam) in combination with a cyclodextrin and/or a carbonate or a bicarbonate. These compositions may be orally administered, for example, to improve the bioavailability or pharmacokinetics of the drug for the treatment of conditions such as pain.

29 Claims, 6 Drawing Sheets

Related U.S. Application Data

(60) Provisional application No. 62/442,136, filed on Jan. 4, 2017, provisional application No. 62/504,105, filed on May 10, 2017, provisional application No. 62/536,466, filed on Jul. 25, 2017.

(51) Int. Cl.
*A61K 31/5415* (2006.01)
*A61P 29/00* (2006.01)
*A61K 47/69* (2017.01)
*A61K 9/00* (2006.01)

(56) References Cited

U.S. PATENT DOCUMENTS

| | | |
|---|---|---|
| 5,872,145 A | 2/1999 | Plachetka |
| 6,060,499 A | 5/2000 | Plachetka |
| 6,077,539 A | 6/2000 | Plachetka et al. |
| 6,479,551 B1 | 11/2002 | Plachetka et al. |
| 6,495,535 B1 | 12/2002 | Plachetka et al. |
| 6,586,458 B1 | 7/2003 | Plachetka |
| 6,926,907 B2 | 8/2005 | Plachetka |
| 7,030,162 B2 | 4/2006 | Plachetka et al. |
| 7,060,694 B2 | 6/2006 | Plachetka et al. |
| 7,332,183 B2 | 2/2008 | Plachetka et al. |
| 8,022,095 B2 | 9/2011 | Plachetka |
| 8,206,741 B2 | 6/2012 | Plachetka |
| 8,512,727 B2 | 8/2013 | Cooper |
| 8,557,285 B2 | 10/2013 | Plachetka |
| 8,852,636 B2 | 10/2014 | Plachetka |
| 8,858,996 B2 | 10/2014 | Plachetka |
| 8,865,190 B2 | 10/2014 | Plachetka |
| 8,945,621 B2 | 2/2015 | Ault et al. |
| 9,161,920 B2 | 10/2015 | Plachetka |
| 9,198,888 B2 | 12/2015 | Plachetka |
| 9,220,698 B2 | 12/2015 | Ault et al. |
| 9,265,732 B2 | 2/2016 | Plachetka et al. |
| 9,345,695 B2 | 5/2016 | Plachetka |
| 9,364,439 B2 | 6/2016 | Plachetka |
| 9,393,208 B2 | 7/2016 | Otult et al. |
| 9,539,214 B2 | 1/2017 | 3Iachetka |
| 9,707,181 B2 | 7/2017 | Plachetka |
| 9,801,824 B2 | 10/2017 | Otult et al. |
| 9,801,827 B2 | 10/2017 | Plachetka et al. |
| 9,821,075 B2 | 11/2017 | Tabuteau |
| 10,029,010 B1 | 7/2018 | Tabuteau |
| 10,058,614 B2 | 8/2018 | Tabuteau |
| 2002/0016348 A1* | 2/2002 | Simitchieva ............ A61K 31/42 514/374 |
| 2007/0281927 A1 | 12/2007 | Tyavanagimatt et al. |
| 2009/0203680 A1 | 8/2009 | Hanna et al. |
| 2010/0226943 A1 | 9/2010 | Brennan et al. |
| 2013/0266658 A1 | 10/2013 | Weiß et al. |
| 2016/0228576 A1 | 8/2016 | Tabuteau |
| 2018/0050106 A1 | 2/2018 | Tabuteau |
| 2018/0207274 A1 | 7/2018 | Tabuteau |
| 2018/0214380 A1 | 8/2018 | Tabuteau |
| 2018/0256593 A1 | 9/2018 | Tabuteau |
| 2018/0264114 A1 | 9/2018 | Tabuteau |
| 2018/0264115 A1 | 9/2018 | Tabuteau |
| 2018/0271981 A1 | 9/2018 | Tabuteau |
| 2018/0280306 A1 | 10/2018 | Tabuteau |
| 2018/0280308 A1 | 10/2018 | Tabuteau |
| 2018/0280512 A1 | 10/2018 | Tabuteau |

FOREIGN PATENT DOCUMENTS

| | | |
|---|---|---|
| CN | 102526058 A | 7/2012 |
| WO | 2000035448 | 6/2000 |
| WO | 2000059475 | 10/2000 |
| WO | 2005076987 | 8/2005 |
| WO | 2005105102 A1 | 11/2005 |
| WO | 2008006216 | 1/2008 |
| WO | 2012072570 | 6/2012 |
| WO | 2014161131 A1 | 10/2014 |
| WO | 2016131067 | 8/2016 |

OTHER PUBLICATIONS

Johnell et al., Concomitant Use of Gastroprotective Drugs Among Elderly NSAID/COX-2 Selective Inhibitor Users: A Nationwide Register-Based Study, Clinical Drug Investigation, 28(11), 687-695, Nov. 2008.
Leonard et al., Proton Pump Inhibitors and Traditional Nonsteroidal Anti-Inflammatory Drugs and the Risk of Acute Interstitial Nephritis and Acute Kidney Injury, Pharmacoepidemiology and Drug Safety, 21(11), 1155-1172, Nov. 2012.
Vonkeman et al., Proton-Pump Inhibitors are Associated with a Reduced Risk for Bleeding and Perforated Gastroduodenal Ulcers Attributable to Non-Steroidal Anti-Inflammatory Drugs: A Nested Case-Control Study, Arthritis Research & Therapy, 9(3), May 2007, 8 pgs.
Yilmaz et al., Does Adding Misoprostol to Standard Intravenous Proton Pump Inhibitor Protocol Improve the Outcome of Aspirin/NSAID-Induced Upper Gastrointestinal Bleeding?, Digestive Diseases and Sciences, 52(1), 110-118, Jan. 2007.
International search report dated Aug. 11, 2016, corresponding to international patent application No. PCT/US2016/026991.
Written opinion of the international searching authority dated Aug. 11, 2016, corresponding to international patent application No. PCT/US2016/026991.
Stella et al., Toxicologic Pathology, 2008, 36:30-42.
Jain et al., AAAPS PharmSciTech, 2011, 12(4):1163-1175.
Baboota et al., Journal of Inclusion Phenomena and Macrocyclic Chemistry, 2005, 51:219-224.
U.S. Appl. No. 15/132,130, filed Apr. 18, 2016 First Named Inventor: Herriot Tabuteau Assignee: Axsome Therapeutics, Inc.
U.S. Appl. No. 15/797,955, filed Oct. 30, 2017 First Named Inventor: Herriot Tabuteau Assignee: Axsome Therapeutics, Inc.
U.S. Appl. No. 15/902,770, filed Feb. 22, 2018 First Named Inventor: Herriot Tabuteau Assignee: Axsome Therapeutics, Inc.
U.S. Appl. No. 15/936,176, filed Mar. 26, 2018 First Named Inventor: Herriot Tabuteau Assignee: Axsome Therapeutics, Inc.
U.S. Appl. No. 15/976,800, filed May 10, 2018 First Named Inventor: Herriot Tabuteau Assignee: Axsome Therapeutics, Inc.
U.S. Appl. No. 15/984,055, filed May 18, 2018 First Named Inventor: Herriot Tabuteau Assignee: Axsome Therapeutics, Inc.
U.S. Appl. No. 15/986,215, filed May 22, 2018 First Named Inventor: Herriot Tabuteau Assignee: Axsome Therapeutics, Inc.
U.S. Appl. No. 15/988,104, filed May 24, 2018 First Named Inventor: Herriot Tabuteau Assignee: Axsome Therapeutics, Inc.
U.S. Appl. No. 15/989,734, filed May 25, 2018 First Named Inventor: Herriot Tabuteau Assignee: Axsome Therapeutics, Inc.
U.S. Appl. No. 16/000,701, filed Jun. 5, 2018 First Named Inventor: Herriot Tabuteau Assignee: Axsome Therapeutics, Inc.
U.S. Appl. No. 16/001,697, filed Jun. 6, 2018 First Named Inventor: Herriot Tabuteau Assignee: Axsome Therapeutics, Inc.
U.S. Appl. No. 16/002,865, filed Jun. 7, 2018 First Named Inventor: Herriot Tabuteau Assignee: Axsome Therapeutics, Inc.
U.S. Appl. No. 16/006,548, filed Jun. 12, 2018 First Named Inventor: Herriot Tabuteau Assignee: Axsome Therapeutics, Inc.
U.S. Appl. No. 16/006,642, filed Jun. 12, 2018 First Named Inventor: Herriot Tabuteau Assignee: Axsome Therapeutics, Inc.
U.S. Appl. No. 16/006,692, filed Jun. 12, 2018 First Named Inventor: Herriot Tabuteau Assignee: Axsome Therapeutics, Inc.
Hosie et al., British Journal of Rheumatology, 35 (suppl.1), 39-43, 1996.
Wojtulewski et al., British Journal of Rheumatology; 35 (suppl.1), 22-28, 1996.
Goldstein et al., Intragastric Acid Control in Non-Steroidal Anti-inflammatory Drug Users: Comparison of Esomeprazole, Lansoprazole and Pantoprazole, Alimentary Pharmacology & Therapeutics 23, 1189-1196, 2006.

(56) References Cited

OTHER PUBLICATIONS

Euller-Ziegler et al. Molexicam: a review of its pharmacokinetics, efficacy and tolerability following intramuscular administration, Inflamm. res. 50, Supplement 1, S5-S9, 2001.

* cited by examiner

PHARMACEUTICAL COMPOSITIONS COMPRISING MELOXICAM

CROSS-REFERENCE TO RELATED APPLICATIONS

This application is a continuation-in-part of PCT/US18/12433, filed Jan. 4, 2018, which claims the benefit of U.S. provisional patent application Nos. 62/442,136, filed Jan. 4, 2017; 62/504,105, filed May 10, 2017; and 62/536,466, filed Jul. 25, 2017, all of which are incorporated by reference herein in their entireties.

BACKGROUND

There continues to be a need for therapies with improved efficacy in treating pain, inflammation, and related conditions.

SUMMARY

This disclosure relates to the use of a bicarbonate and/or a cyclodextrin, such as sulfobutylether β-cyclodextrin (SBEβCD), to improve the pharmacokinetics or bioavailability of a drug, such as a nonsteroidal anti-inflammatory drug (NSAID), e.g. meloxicam, a triptan, e.g. rizatriptan, or a combination thereof.

For example, some embodiments include dosage forms comprising a triptan (such as rizatriptan or frovatriptan), in combination with a cyclodextrin (optionally as an inclusion complex of the triptan and the cyclodextrin), and/or a bicarbonate, and methods of treatment using the dosage form.

Some embodiments include a dosage form comprising: meloxicam; a sulfobutyl ether β-cyclodextrin (SBEβCD); a bicarbonate; and a triptan wherein the dosage form is an oral dosage form having a shorter $T_{max}$ of meloxicam than a reference dosage form that: 1) contains the same amount of meloxicam, 2) does not contain a SBEβCD, and 3) does not contain a bicarbonate.

Some embodiments include an inclusion complex of a triptan such as rizatriptan or frovatriptan in a cyclodextrin.

Some embodiments include a dosage form comprising: 1) an inclusion complex of a triptan, such as rizatriptan or frovatriptan, and a cyclodextrin, or 2) a triptan, such as rizatriptan or frovatriptan, and a carbonate or a bicarbonate.

Some methods include administration of a product that contains a combination of a triptan with: 1) a cyclodextrin and/or 2) a buffering agent. In some embodiments, the method involves treating a patient with a pharmaceutical formulation comprising a triptan, such as rizatriptan or frovatriptan, and a cyclodextrin and/or a carbonate/bicarbonate. Some embodiments may also include increasing the bioavailability of a triptan, such as rizatriptan or frovatriptan, or increasing the rate at which the triptan becomes bioavailable in a subject in need thereof as compared to a formulation without a cyclodextrin or carbonate/bicarbonate.

Some embodiments include a method of improving the pharmacokinetics of a triptan or an NSAID, comprising orally administering a dosage form described herein to a mammal or human being in need of treatment with the triptan or the NSAID.

Some embodiments include a method of treating pain, comprising orally administering a dosage form described herein to a mammal or human being in need thereof.

DETAILED DESCRIPTION

Figure 1:
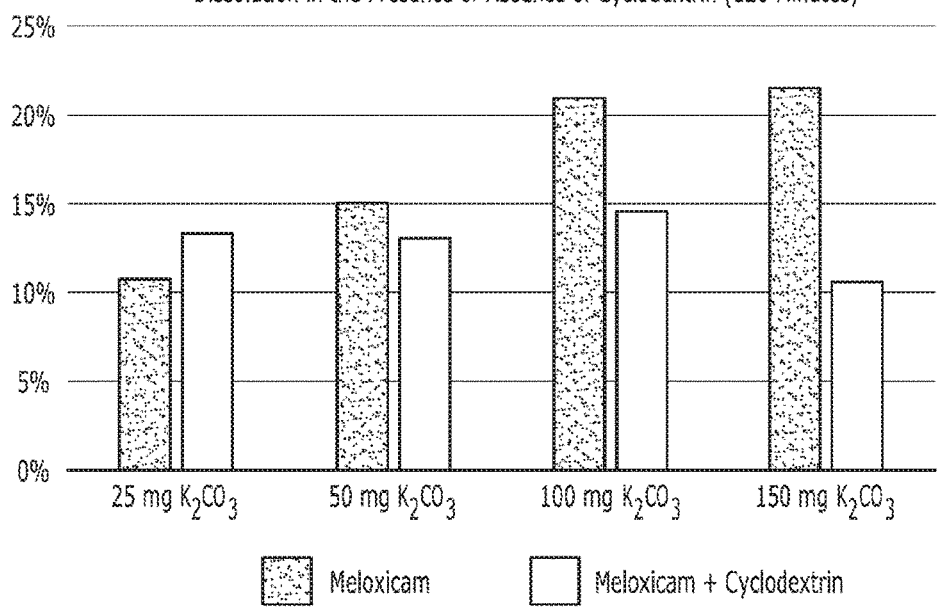
FIG. 1 is a depiction of the results described in Example 2 and contained in Table 6.
Figure 2:
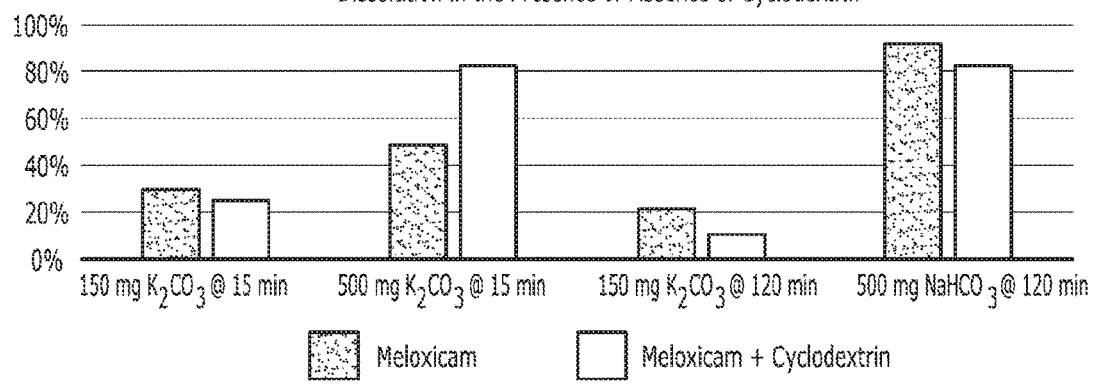
FIG. 2 is another depiction of the results described in Example 2 and contained in Table 6.
Figure 3:
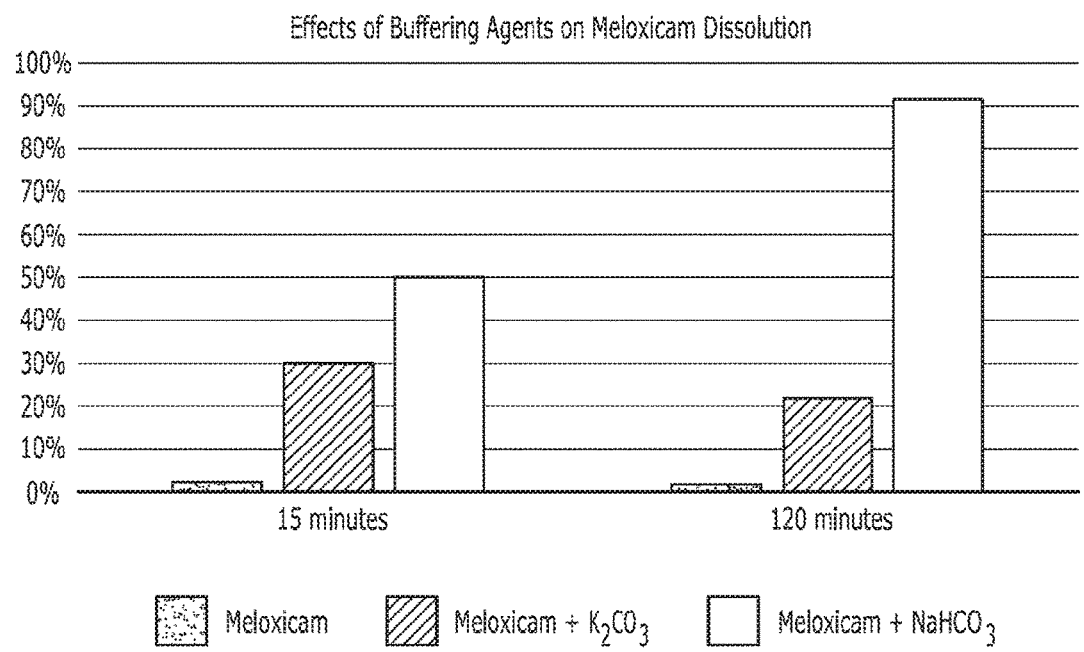
FIG. 3 is another depiction of the results described in Example 2 and contained in Table 6.
Figure 4:
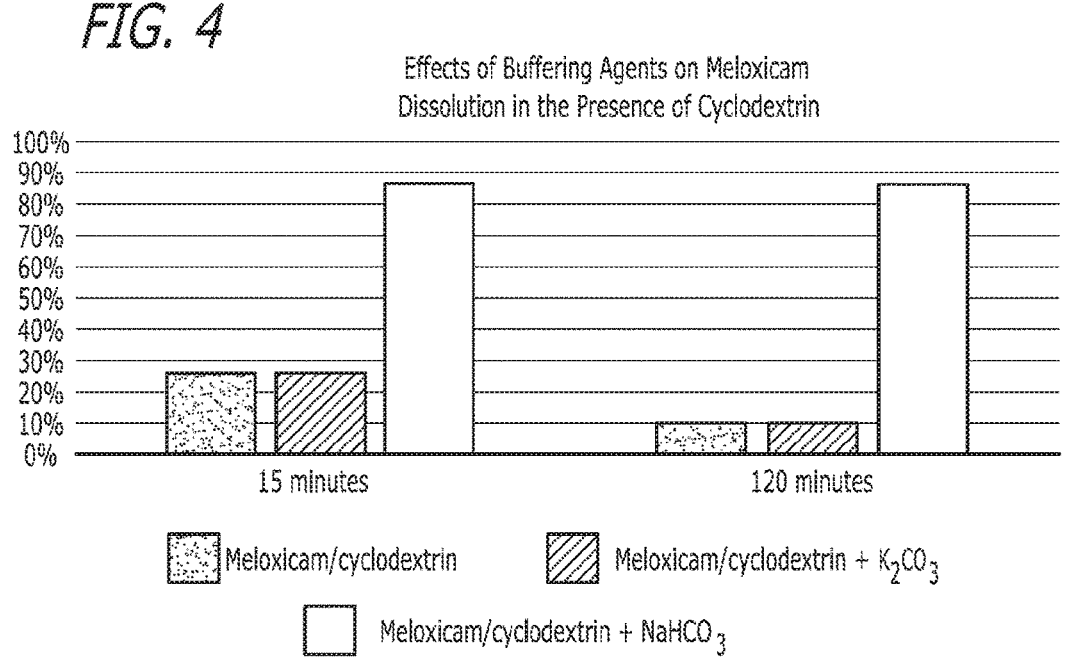
FIG. 4 is another depiction of the results described in Example 2 and contained in Table 6.
Figure 5:
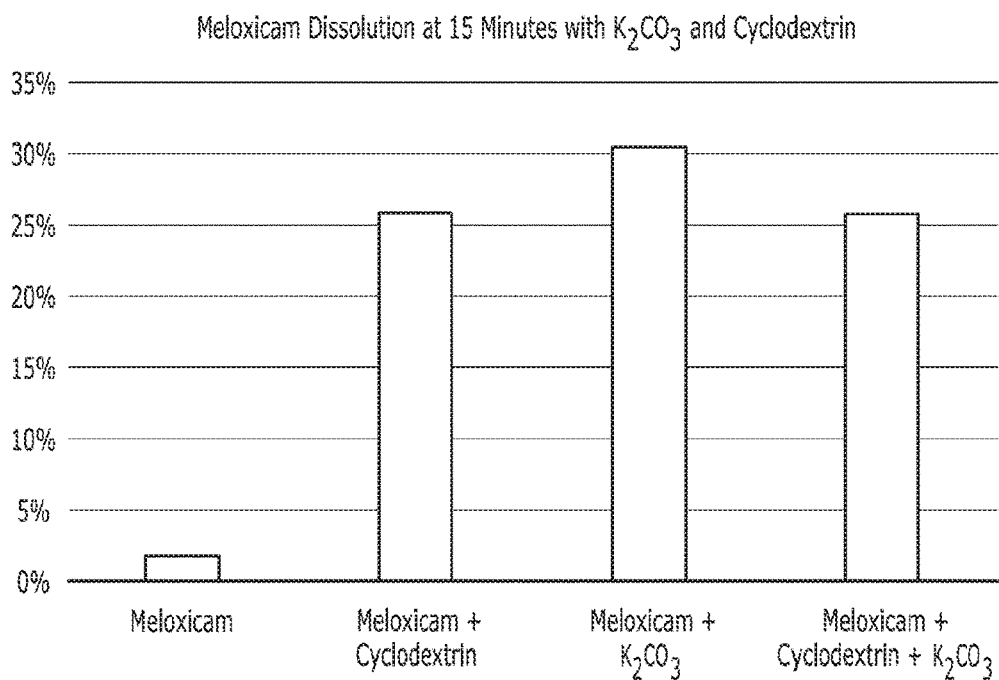
FIG. 5 is another depiction of the results described in Example 2 and contained in Table 6.
Figure 6:
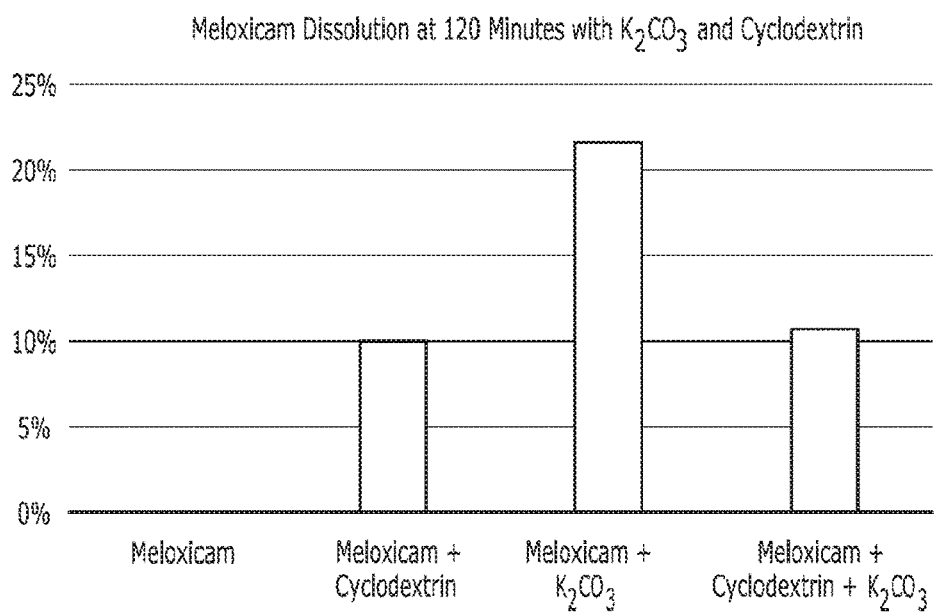
FIG. 6 is another depiction of the results described in Example 2 and contained in Table 6.
Figure 7:
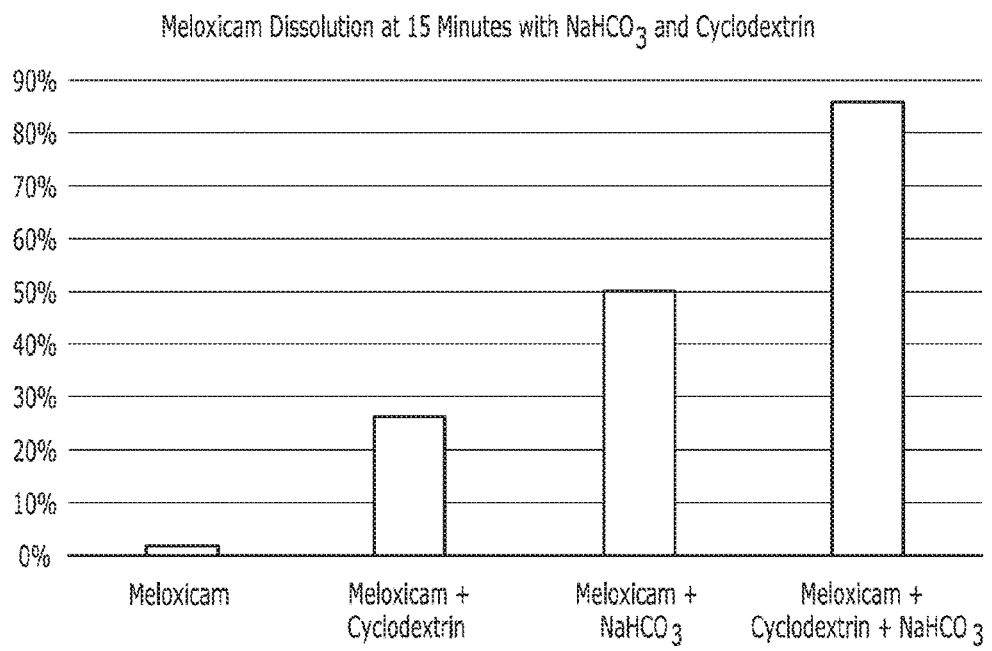
FIG. 7 is another depiction of the results described in Example 2 and contained in Table 6.
Figure 8:
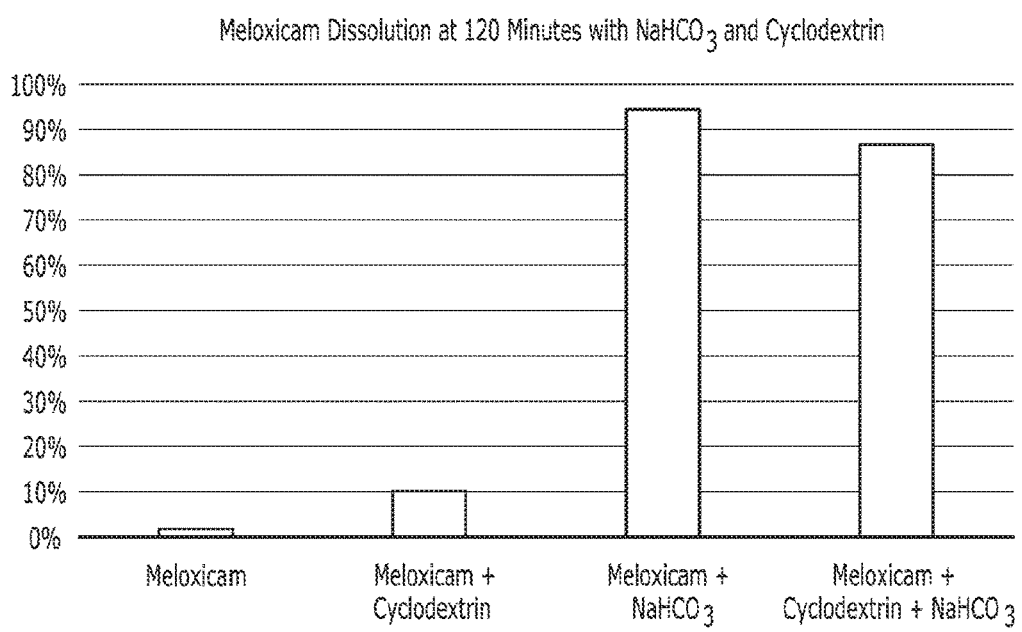
FIG. 8 is another depiction of the results described in Example 2 and contained in Table 6.
Figure 9:
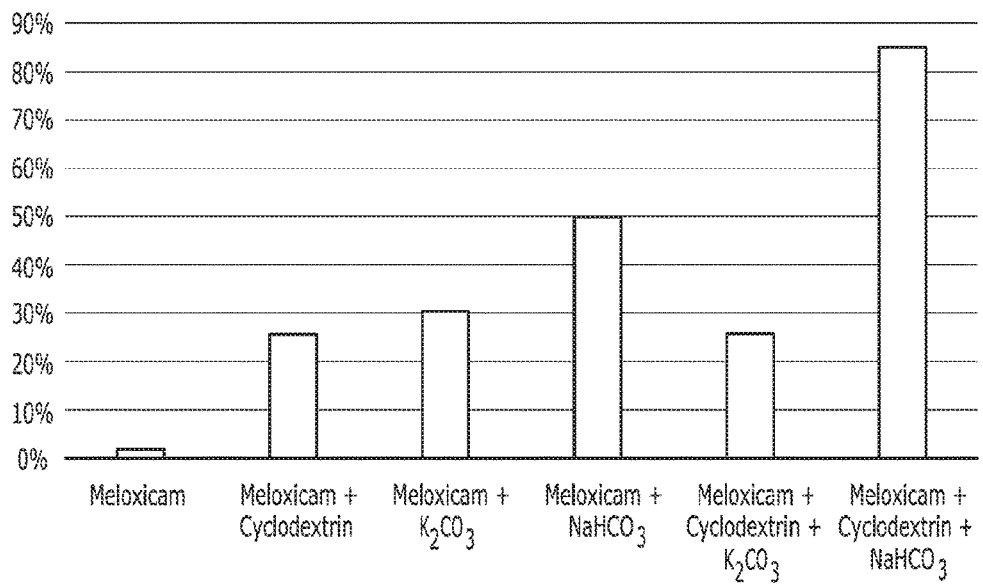
FIG. 9 is another depiction of the results described in Example 2 and contained in Table 6.
Figure 10:
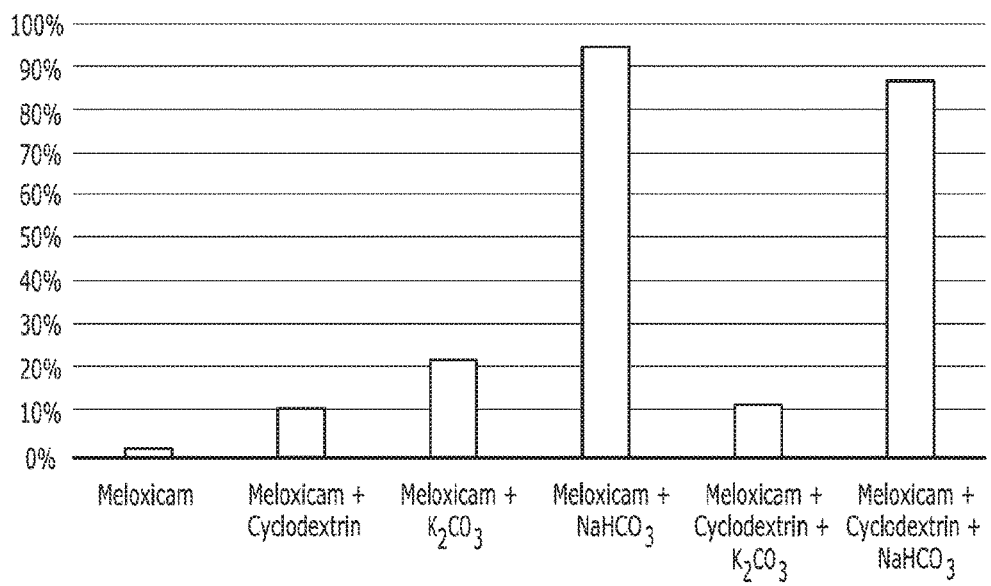
FIG. 10 is another depiction of the results described in Example 2 and contained in Table 6.

Meloxicam and some other NSAIDs, and other drugs, have poor aqueous solubility which may reduce bioavailability and slow the onset of pain relief. One method of increasing the solubility and bioavailability of meloxicam or another drug is through the use of cyclodextrins in combination with meloxicam.

Generally, this may be accomplished using a dosage form, such as an oral dosage form, containing a triptan (such as rizatriptan), optionally in combination with an NSAID (such as meloxicam), and 1) a cyclodextrin (optionally in an inclusion complex), and/or 2) a buffering agent, such as a bicarbonate. Administering this type of dosage form to a patient may increase the bioavailability of the triptan (e.g. rizatriptan) or the NSAID (e.g. meloxicam) in the patient or increase the rate at which the triptan (e.g. rizatriptan) or the NSAID (e.g. meloxicam) becomes bioavailable, or increase the rate at which the plasma concentration of the triptan or the NSAID increases. For example, the triptan or the NSAID may have a shorter $T_{max}$, or may have an increased $C_{max}$ or area under the plasma concentration curve (AUC) as a result of the administration of this type of dosage form.

Any suitable triptan may be used, such as sumatriptan, rizatriptan, naratriptan, eletriptan, donitriptan, almotriptan, frovatriptan, alvitriptan, zolmatriptan, etc., including combinations or salts thereof. In some embodiments, the triptan comprises rizatriptan, which has the structure as shown below.

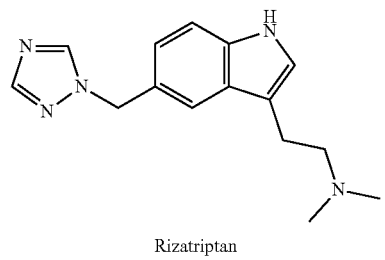 [SMILES: CN(C)CCc1c[nH]c2ccc(Cn3cncn3)cc12]

Rizatriptan

The NSAID may include, but is not limited to, celecoxib, rofecoxib, lumiracoxib, valdecoxib, parecoxib, etoricoxib, CS-502, JTE-522, L-745,337, NS398, aspirin, acetaminophen (considered to be an NSAID for the purposes of the present disclosure), ibuprofen, flurbiprofen, ketoprofen, naproxen, oxaprozin, etodolac, indomethacin, ketorolac, lornoxicam, meloxicam, piroxicam, droxicam, tenoxicam, nabumetone, diclofenac, meclofenamate, mefenamic acid, diflunisal, sulindac, tolmetin, fenoprofen, suprofen, benoxaprofen, aceclofenac, tolfenamic acid, oxyphenbutazone, azapropazone, phenylbutazone, or combinations thereof.

In some embodiments, the NSAID is meloxicam, which has the structure:

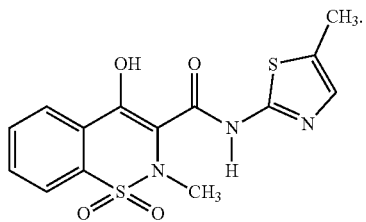 [SMILES: Cc1cnc(NC(=O)C2=C(O)c3ccccc3S(=O)(=O)N2C)s1]

Meloxicam exhibits anti-inflammatory, analgesic, and antipyretic activities. The meloxicam mechanism of action may be related to the inhibition of prostaglandin synthetase (cyclo-oxygenase, COX) which is involved in the initial steps of the arachidonic acid cascade, resulting in the reduced formation of prostaglandins, thromboxanes and prostacylin.

A dosage form may be given enterally including, but not limited to, oral, sublingual, or rectal delivery, or parenterally including, but not limited to, intravenous, intramuscular, intranasal, or subcutaneous delivery.

The term "treating" or "treatment" broadly includes any kind of treatment activity, including the diagnosis, cure, mitigation, or prevention of disease in man or other animals, or any activity that otherwise affects the structure or any function of the body of man or other animals.

The dosage form may be used to treat, or provide relief of, any type of pain including, but not limited to, migraine and other types of headache, inflammatory pain, musculoskeletal pain, neuropathic pain, chronic pain, acute pain, localized pain, systemic pain, cancer-related pain, acute pain, pain due to injury, pain due to illness (e.g., fever), post-operative pain, etc. In some instances, pain relief may be palliative, or pain relief may be provided independent of improvement of the disease or condition or the underlying cause of the disease or condition. For example, although the underlying disease may not improve, or may continue to progress, an individual suffering from the disease may experience pain relief. In some embodiments, the pain affects a muscle, nerve, cartilage, bone, ligament, tendon, tendon sheaths, bursae, or joint.

Migraine is a headache disorder characterized by recurrent headaches that may be moderate to severe. The headaches may affect one half of the head, may be pulsating in nature, and may last from 2 to 72 hours. Associated symptoms may include nausea, vomiting, and sensitivity to light (photophobia), sound (phonophobia), or smell. The pain can be made worse by physical activity. Migraines may be associated with an aura, which may be a short period of visual disturbance which signals that the headache will soon occur.

In some methods, the dosage form may be administered to relieve inflammatory pain, including inflammatory musculoskeletal pain, pain due to injury, arthritis pain, and complex regional pain syndrome. In other embodiments, the inflammatory pain may be chronic or acute.

In some embodiments, the dosage form (e.g. a dosage form containing a triptan such as rizatriptan or frovatriptan, and/or an NSAID such as meloxicam) may be administered to relieve arthritis pain, or other signs and/or symptoms of arthritis. Arthritis refers to inflammatory joint diseases that can be associated with pain. Examples of arthritis include, but are not limited to, rheumatoid arthritis, juvenile rheumatoid arthritis (pauciarticular and polyarticular course), osteoarthritis, erosive osteoarthritis, sero-negative (non-rheumatoid), arthropathies, non-articular rheumatism, peri-articular disorders, axial spondyloarthritis, transient osteoarthritis of the hip, vertebral crush fractures, arthritis associated with osteoporosis, and neuropathic arthropathies including Charcot's foot, axial spondyloarthritis including ankylosing spondylitis, and SAPHO syndrome. In other embodiments, the arthritis pain may be chronic or acute. In some embodiments the dosage form may be administered to relief the signs and/or symptoms of an arthritis including but not limited to osteoarthritis.

In some embodiments, the dosage form (e.g. a dosage form containing a triptan such as rizatriptan or frovatriptan, and/or an NSAID such as meloxicam) may be administered to relieve neuropathic pain, including diabetic peripheral neuropathy, post-herpetic neuralgia, trigeminal neuralgia, monoradiculopathies, phantom limb pain, sciatica, pudendal neuralgia, and central pain. Other causes of neuropathic pain may include, but are not limited to, cancer-related pain, lumbar nerve root compression, spinal cord injury, post-stroke pain, central multiple sclerosis pain, HIV-associated neuropathy, and radio-therapy or chemo-therapy associated neuropathy. The neuropathic pain may be chronic or acute.

For some methods, the dosage form (e.g. a dosage form containing a triptan such as rizatriptan or frovatriptan, and/or an NSAID such as meloxicam) may be administered to relieve musculoskeletal pain. Examples of musculoskeletal pain may include, but are not limited to, back pain, low back pain (e.g., lumbosacral pain), neck pain, infection, cramps, tendonitis, epidondylitis, carpal tunnel syndrome, joint pain, fibromyalgia, pain due to injury, Tunnel syndromes, pain associated with bone fractures, sprains, fibrous dysplasia, osteogenesis imperfecta, Paget's disease of bone, transient osteoporosis, and transient osteoporosis of the hip. In other embodiments, the musculoskeletal pain may be chronic or acute.

For some methods, administration of the dosage form (e.g. a dosage form containing a triptan such as rizatriptan or frovatriptan, and/or an NSAID such as meloxicam) may achieve a reduction in pain that lasts at least about one hour, at least about two hours, at least about three hours, at least about four hours, at least about six hours, at least about eight hours, about 8 to about 24 hours, or about 24 hours. In other embodiments, administration of the dosage form may achieve a reduction in pain that is observed at about 10 minutes, at about 30 minutes, at about one hour, at about two hours, at about three hours, at about four hours, at about five hours, at about six hours, at or less than about 5, 10, 15, 20, 25, 30, 35, 40, 45, 50, or 60 minutes, at two hours or less, at three hours or less, or other time period bound by these ranges, after administration of the dosage form.

A human being that is treated for a disease or condition with any of the dosage forms described herein (e.g. a dosage form containing a triptan such as rizatriptan or frovatriptan, and/or an NSAID such as meloxicam) may be of any age. For example the person may have an age of about 10-90 years, about 20-80 years, about 30-75 years, about 40-70 years, about 1-16 years, about 80-95 years, about 18 years or more, about 20 years or more, about 25 years or more, about 30 years or more, about 40 years or more, about 45 years or more, about 50 years or more, about 55 years or more, about 60 years or more, about 65 years or more, or any other age in a range bounded by, or between, any of these values.

In some embodiments, a human being that is treated for a disease or condition with a dosage form (e.g. a dosage form containing a triptan such as rizatriptan or frovatriptan, and/or an NSAID such as meloxicam) has suffered from the pain or condition associated with the pain for at least 1 day, at least one week, at least 2 weeks, at least 1 month, at least 6 weeks, at least 2 months, at least 3 months, at least 6 months, at least 1 year, at least 5 years, at least 10 years, at least 15 years, at least 20 years, at least 30 years, at least 40 years, at least 50 years or any duration in a range bounded by, or between, any of these values.

A cyclodextrin used in a dosage form with a drug (including meloxicam or another NSAID, rizatriptan, frovatriptan, or another triptan) could include a cyclodextrin, a cyclodextrin derivative, and/or a salt thereof. Cyclodextrins (also known as cycloamyloses) are generally cyclic polysaccharides which form a bucket-like shape. Cyclodextrins help to increase bioavailability of other molecules because cyclodextrins are hydrophobic on the inside and hydrophilic on the outside which helps to facilitate the transport of hydrophobic molecules to a hydrophilic medium. The naturally occurring cyclodextrins include six, seven, and eight glucose units (α, β, and γ-cyclodextrin, respectively). However, synthetic cyclodextrins containing more or less glucose units are possible. In aqueous solutions, cyclodextrins can form complexes (i.e., an inclusion complex) with drugs by incorporating the drug into the center/hydrophobic portion of the cyclodextrin ring; although cyclodextrins are also known to aggregate around a drug in a micelle-type structure. This ability of cyclodextrins may allow them to act as carriers of less soluble drugs to increase the drugs' bioavailability.

An inclusion complex of drug (including meloxicam or another NSAID, rizatriptan, frovatriptan, or another triptan) and cyclodextrin may be more water-soluble relative to the non-complexed drug. The cyclodextrin may be a naturally-occurring cyclodextrin (e.g., α, β, or γ-cyclodextrin) or a synthetic cyclodextrin. In some embodiments, α-cyclodextrins, derivatives, or salts thereof may be used. α-Cyclodextrins may include, but are not limited to, (2,3,6-tri-O-acetyl)-α-cyclodextrin, (2,3,6-tri-O-methyl)-α-cyclodextrin, (2,3,6-tri-O-octyl)-α-cyclodextrin, 6-bromo-6-deoxy-α-cyclodextrin, 6-iodo-6-deoxy-α-cyclodextrin, (6-O-tertbutyl-dimethylsilyl)-α-cyclodextrin, butyl-α-cyclodextrin, succinyl-α-cyclodextrin, (2-hydroxypropyl)-α-cyclodextrin, or combinations thereof.

In some embodiments, β-cyclodextrins, derivatives, or salts thereof may be used. β-cyclodextrins may include, but are not limited to, hydroxypropyl-β-cyclodextrin, 6-monodeoxy-6-monoamino-β-cyclodextrin, glucosyl-β-cyclodextrin, maltosyl-β-cyclodextrin, 6-O-α-D-glucosyl-β-cyclodextrin, 6-O-α-maltosyl-β-cyclodextrin, 6-azido-6-deoxy-β-cyclodextrin, (2,3-di-O-acetyl-6-O-sulfo)-β-cyclodextrin, methyl-β-cyclodextrin, dimethyl-β-cyclodextrin (DMβCD), trimethyl-β-cyclodextrin (TMβCD), (2,3-di-O-methyl-6-O-sulfo)-β-cyclodextrin, (2,6-di-O-methyl)-β-cyclodextrin, (2,6-di-O-ethyl)-β-cyclodextrin, (2,3,6-tri-O-methyl)-β-cyclodextrin, (2,3,6-tri-O-acetyl)-β-cyclodextrin, -(2,3,6-tri-O-benzoyl)-β-cyclodextrin, (2,3,6-tri-O-ethyl)-β-cyclodextrin, 6-iodo-6-deoxy-β-cyclodextrin, 6-(dimethyl-tert-butylsilyl)-6-deoxy-β-cyclodextrin, 6-bromo-6-deoxy-β-cyclodextrin, monoacetyl-β-cyclodextrin, diacetyl-β-cyclodextrin, triacetyl-β-cyclodextrin, (3-O-acetyl-2,6-di-O-methyl)-β-cyclodextrin, (6-O-maltosyl)-β-cyclodextrin, (6-O-sulfo)-β-cyclodextrin, (6-O-t-butyldimethylsilyl-2,3-di-O-acetyl)-β-cyclodextrin, succinyl-(2-hydroxypropyl)-β-cyclodextrin, (2,6-di-O-)ethyl-β-cyclodextrin, (2-carboxyethyl)-β-cyclodextrin (CMEβCD), hydroxyethyl-β-cyclodextrin (HEβCD), (2-hydroxypropyl)-β-cyclodextrin, (2-hydroxypropyl)-β-cyclodextrin (HPβCD), (3-hydroxypropyl)-β-cyclodextrin (3HPβCD), (2,3-hydroxypropyl)-β-cyclodextrin (DHPβCD), butyl-β-cyclodextrin, methyl-β-cyclodextrin, silyl((6-O-tert-butyldimethyl)-2,3,-di-O-acetyl)-β-cyclodextrin, succinyl-β-cyclodextrin, (2-hydroxyisobutyl)-β-cyclodextrin, randomly methylated-β-cyclodextrin, branched-β-cyclodextrin, or combinations thereof.

In other embodiments, a β-cyclodextrin may be a sulfoalkyl ether cyclodextrin, derivative, or salt thereof. Examples of sulfoalkyl ether cyclodextrin derivatives may include, but are not limited to, sulfobutyl ether-β-cyclodextrin (e.g., SBEβCD, betadex, CAPTISOL®). In some embodiments, a SBEβCD may have about 4-8, about 5-8, about 4-7, about 6-7, or about 6.5 sulfobutyl ether groups per cyclodextrin molecule.

In some embodiments, γ-cyclodextrins, derivatives, or salts thereof may be used. γ-cyclodextrins may include carboxymethyl-γ-cyclodextrin, (2,3,6-tri-O-acetyl)-γ-cyclodextrin, (2,3,6-tri-O-methyl)-γ-cyclodextrin, (2,6-di-O-pentyl)-γ-cyclodextrin, 6-(dimethyl-tert-butylsilyl)-6-deoxy-γ-cyclodextrin, 6-bromo-6-deoxy-γ-cyclodextrin, 6-iodo-6-deoxy-γ-cyclodextrin, (6-O-t-butyldimethylsilyl)-γ-cyclodextrin, succinyl-γ-cyclodextrin, hydroxypropyl-γ-cyclodextrin, (2-hydroxypropyl)-γ-cyclodextrin, acetyl-γ-cyclodextrin, butyl-γ-cyclodextrin, or combinations thereof.

In some embodiments, the dosage form may include a bicarbonate, such as sodium bicarbonate, potassium bicarbonate, etc. A bicarbonate may help to increase the pharmacokinetics or bioavailability of meloxicam or another drug, such as rizatriptan.

In some embodiments, enhanced bioavailability of a drug, such as meloxicam or a triptan (e.g. rizatriptan) in the dosage form may be achieved by administering a dosage form comprising a salt form of the drug, by generating an inclusion complex of the drug with cyclodextrin, and/or by including a bicarbonate. This may allow a reduced molar amount of the drug to be used as compared to other dosage forms containing the drug in treating diseases or disorders.

Unless otherwise indicated, any reference to a compound herein, such as meloxicam, an NSAID, a triptan, rizatriptan, or a cyclodextrin, by structure, name, or any other means, includes pharmaceutically acceptable salts, alternate solid forms, such as polymorphs, solvates, hydrates, enantiomers, tautomers, deuterium-modified forms, or any other chemical species, such as precursors, prodrugs, or any other chemical species that may rapidly convert to a compound described herein under conditions in which the compounds are used as described herein.

In some embodiments, use of a cyclodextrin or a bicarbonate may improve the oral bioavailability (e.g. a higher $C_{max}$ and/or higher AUC) of meloxicam in a subject (human or animal) by at least about 10%, at least about 20%, at least about 30%, at least about 40%, at least about 50%, at least about 60%, at least about 70%, at least about 80%, at least about 90%, up to about 100%, up to about 200%, or any amount in a range bounded by, or between, any of these values as compared to administration of meloxicam alone.

In some embodiments, use of a cyclodextrin or a bicarbonate may improve the oral bioavailability (e.g. a higher $C_{max}$ and/or higher AUC) of a triptan such as rizatriptan or frovatriptan in subject (human or animal) by at least about 10%, at least about 20%, at least about 30%, at least about 40%, at least about 50%, at least about 60%, at least about 70%, at least about 80%, at least about 90%, up to about 100%, up to about 200%, or any amount in a range bounded by, or between, any of these values as compared to administration of the triptan alone.

Due to the improved bioavailability as described above, the dosage form may contain, or a subject may receive, on a molar basis, less of the drug, such as a triptan (e.g. rizatriptan or frovatriptan) or an NSAID (e.g. meloxicam) than would otherwise be administered of the drug alone. For example, a dosage form may contain, or a mammal may receive, at least about 10 mole % less, at least about 20 mole % less, at least about 30 mole % less, at least about 40 mole % less, at least about 50 mole % less, at least about 60 mole % less, at least about 70 mole % less, at least about 80 mole % less, at least about 85 mole % less, and/or up to about 90 mole % less, 95 mole % less, 98 mole % less, or any amount in a range bounded by, or between, any of these values of meloxicam as that would otherwise be administered of meloxicam alone.

In other embodiments, use of other NSAIDs, opioids, or other pain medications may be reduced by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, up to about 100%, or any amount in a range bounded by, or between, any of these values when administered with a drug such as an triptan (e.g. rizatriptan) or an NSAID (e.g. meloxicam), with a cyclodextrin and/or a bicarbonate, as compared to administration of the NSAID, the opioid or the other pain medication alone.

In some embodiments, a dosage form may contain an NSAID, such as celecoxib, rofecoxib, lumiracoxib, valdecoxib, parecoxib, etoricoxib, CS-502, JTE-522, L-745,337, NS398, aspirin, acetaminophen (considered to be an NSAID for the purposes of the present disclosure), ibuprofen, flurbiprofen, ketoprofen, naproxen, oxaprozin, etodolac, indomethacin, ketorolac, lornoxicam, piroxicam, droxicam, tenoxicam, nabumetone, diclofenac, meclofenamate, mefenamic acid, diflunisal, sulindac, tolmetin, fenoprofen, suprofen, benoxaprofen, aceclofenac, tolfenamic acid, oxyphenbutazone, azapropazone, phenylbutazone, in an amount of about 1-1000 mg, about 1-500 mg, about 1-400 mg, about 1-300 mg, about 1-200 mg, about 1-100 mg, about 1-50 mg, about 1-10 mg, about 1-5 mg, about 2-6 mg, about 3-7 mg, about 4-8 mg, about 5-10 mg, about 7-12 mg, about 5-15 mg, about 10-20 mg, about 15-25 mg, about 20-30 mg, about 25-35 mg, about 30-40 mg, about 35-45 mg, about 40-50 mg, about 50-150 mg, about 50-100 mg, about 100-200 mg, about 150-250 mg, about 200-300 mg, about 250-350 mg, about 300-400 mg, about 350-450 mg, about 400-500 mg, about 100 mg, about 200 mg, about 325 mg, or any amount in a range bounded by, or between, any of these values. These doses may be a safe dose for repeated administration, such as 1, 2, 3, or 4 times a day, or repeated at an interval of 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, about 1 week, about 4 weeks, about 6 weeks, about 1-2 months, about 6 weeks, about 2-3 months, about 3-4 months, about 4-5 months, about 5-6 months, about 6-7 months, about 7-8 months, about 8-9 months, about 9-10 months, about 10-11 months, about 11-12 months, about 2 years, etc.

In some embodiments, a dosage form may contain meloxicam in an amount of about 1-50 mg; about 1-10 mg; about 1-5 mg; about 10-40 mg; about 1-35 mg; about 2-6 mg, about 3-7 mg, about 4-8 mg, about 5-10 mg, about 7-12 mg, about 5-15 mg, about 10-20 mg, about 10-30 mg, about 18-22 mg, about 19-21 mg, about 15-25 mg, about 20-30 mg, about 25-35 mg, about 30-40 mg, about 35-45 mg, about 40-50 mg, about 1-25 mg; about 1-15 mg; about 5-20 mg; about 5 mg; about 7.5 mg; about 10 mg; about 15 mg; about 20 mg; about 30 mg; or any amount in a range bounded by, or between, any of these values. For any amounts of meloxicam (or any other compound) described herein, salt forms of meloxicam (or another compound) may be present in the amounts recited above, or amounts that are molar equivalents to these amounts for the non-salt form of meloxicam (or another compound). These doses may be a safe dose for repeated administration, such as 1, 2, 3, or 4 times a day, or repeated at an interval of 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, about 1-2 months, about 4 weeks, about 6 weeks, about 2-3 months, about 3-4 months, about 4-5 months, about 5-6 months, about 6-7 months, about 7-8 months, about 8-9 months, about 9-10 months, about 10-11 months, about 11-12 months, about 2 years, etc.

For some dosage forms, a drug (such as meloxicam, frovatriptan, or rizatriptan) forms a complex with the substituted-β-cyclodextrin or other cyclodextrin which may be formulated into a solid dosage form. Such a dosage form may be suitable for oral administration. A drug-cyclodextrin inclusion complex may also be dissolved in water or another solvent to form a parenteral formulation. However, physical mixtures of drug and the substituted-β-cyclodextrin or other cyclodextrins that are not inclusion complexes may also be used in oral or parenteral dosage forms.

Formation of an inclusion complex of a drug (such as meloxicam, frovatriptan, or rizatriptan) and a cyclodextrin may help to improve the properties of a dosage form. For some inclusion complexes, the drug and the cyclodextrin (e.g., SBEβCD) may have a molar ratio of about 0.5-2 (a molar ratio of 0.5 is 0.5 moles of the drug to 1 mole of cyclodextrin), about 0.5-0.7, about 0.6-0.8, about 0.7-0.9, about 0.8-1, about 0.9-1.1, about 1-1.2, about 1.1-1.3, about 1.2-1.4, about 1.3-1.5, about 1.4-1.6, about 1.5-1.7, about 1.6-1.8, about 1.7-1.9, about 1.8-2, about 1.9-2.1, about 2-2.2, about 0.8-1.2, about 1, or any ratio in a range bounded by any of these values.

In some embodiments, an inclusion complex is formed by (1) mixing a homogeneous solution of a drug such as meloxicam or a triptan with a homogeneous solution of the cyclodextrin to form a homogeneous solution of the drug and the cyclodextrin, and (2) removing or evaporating the solvent of the homogeneous solution of the drug and the cyclodextrin to form the complex comprising the inclusion complex of the drug in a cyclodextrin. In some embodiments, the solutions can be pH-adjusted aqueous solutions. The pH can be adjusted using a buffering agent. In some embodiments, the solvent can be removed or evaporated by lyophilization, spray drying, or any other means that is suitable. In some embodiments, the solvent can be removed by vacuum drying, etc.

For some dosage forms, a cyclodextrin (e.g., SBEβCD) may be employed in a weight ratio to the meloxicam within the range of about 1-1000 (e.g. 1 g of cyclodextrin per 1 g of meloxicam is a weight ratio of 1); about 1-500, about 1-5, about 1-20; about 1-10; about 1-15; about 2-4, about 3-5, about 4-6, about 5-7, about 6-8, about 7-9, about 8-10, about 0.01-1; about 0.05-1; about 0.1-1; about 0.2-1; about 0.3-1, about 0.4-1, about 0.5-1, about 0.6-1, about 0.7-1, about 0.8-1, or any weight ratio in a range bounded by, or between, any of these values. Each type of cyclodextrin employed may have a different weight ratio to the meloxicam in the dosage form.

For some dosage forms, a cyclodextrin (e.g., SBEβCD) may be employed in a weight ratio to the triptan, e.g. rizatriptan or frovatriptan, within the range of about 1-1000 (e.g. 10 g of cyclodextrin per 1 g of rizatriptan or frovatriptan is a weight ratio of 10); about 1-500; about 1-100; about 1-50; about 1-20; about 1-10; about 1-15; about 1-5, about 2-4, about 3-5, about 4-6, about 5-7, about 6-8, about 7-9, about 8-10, about 0.01-1; about 0.05-1; about 0.1-1; about 0.2-1; about 0.3-1; about 0.4-1; about 0.5-1; about 0.6-1; about 0.7-1; about 0.8-1; or any weight ratio in a range bounded by, or between, any of these values. Each type of cyclodextrin employed may have a different weight ratio to the triptan in the dosage form.

For some dosage forms, a cyclodextrin (e.g., SBEβCD) may be employed in a weight ratio to rizatriptan within the range of about 1-1000 (e.g. 10 g of cyclodextrin per 1 g of rizatriptan is a weight ratio of 10); about 1-500; about 1-100; about 1-50; about 1-20; about 1-10; about 1-15; about 2-4, about 3-5, about 4-6, about 5-7, about 6-8, about 7-9, about 8-10, about 9-11, about 10-12, about 11-13, about 12-14, about 13-15, about 14-16, about 15-17, about 16-18, about 17-19, about 18-20, about 19-21, about 0.001-1; about 0.01-1; about 0.05-1; about 0.1-1; about 0.2-1; about 0.3-1, about 0.4-1, about 0.5-1, about 0.6-1, about 0.7-1, about 0.8-1, or any weight ratio in a range bounded by, or between, any of these values. Each type of cyclodextrin employed may have a different weight ratio to rizatriptan in the dosage form.

In some embodiments; a dosage form may contain rizatriptan in an amount of about 1-50 mg; about 1-10 mg; about 20-30 mg; about 30-40 mg; or about 40-50 mg; about 10-40 mg; about 1-35 mg; about 1-25 mg; about 1-15 mg; about 5-20 mg; about 1-50 mg; about 1-5 mg; about 1-10 mg; about 5-20 mg; about 1-50 mg; about 1-5 mg; about 2-6 mg; about 3-7 mg; about 4-8 mg; about 5-10 mg; about 6-11 mg; about 7-12 mg; about 8-13 mg; about 9-11 mg; about 9-14 mg; about 10-15 mg; about 11-16 mg; about 12-17 mg; about 13-18 mg; about 14-19 mg; about 15-20 mg; about 5-15 mg; about 10-20 mg; about 20-30 mg; about 30-40 mg; about 40-50 mg; about 0.5 mg; about 1 mg; about 1.5 mg; about 2 mg; about 2.5 mg; about 3 mg; about 3.5 mg; about 4 mg; about 4.5 mg; about 5 mg; about 6 mg; about 7 mg; about 7.5 mg; about 10 mg; about 15 mg; about 30 mg; or any amount in a range bounded by, or between, any of these values.

For any amounts of rizatriptan described herein, salt forms of rizatriptan may be present in the amounts recited above, or amounts that are molar equivalents to these amounts for the rizatriptan free base. For example, assuming that the molecular weight of rizatriptan free base is 269.3 g/mol, 10 mg of rizatriptan is 37.1 mmol of rizatriptan. Thus, a molar equivalent of 10 mg of rizatriptan free base would be the mass of 37.1 mmol of that salt form. For example, for the benzoate salt (mw=391.2 g/mol), the molar equivalent of 10 mg of the free base (or 37.1 mmol), would be 14.5 mg. These doses may be a safe dose for repeated administration, such as 1, 2, 3, or 4 times a day, or repeated at an interval of 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 4 weeks, 4-6 weeks, about 1-2 months, about 6 weeks, about 2-3 months, about 3-4 months, about 4-5 months, about 5-6 months, about 6-7 months, about 7-8 months, about 8-9 months, about 9-10 months, about 10-11 months, about 11-12 months, etc.

The other triptans may be administered to patients at any dosages effective at relieving pain. In some embodiments, the dosage form may contain the triptan in any amount in a range bounded by any of the values described above.

In some embodiments, a dosage form may contain frovatriptan or another triptan in an amount of about 1-50 mg; about 1-10 mg; about 20-30 mg; about 30-40 mg; or about 40-50 mg; about 10-40 mg; about 1-35 mg; about 1-25 mg; about 1-15 mg; about 5-20 mg; about 1-5 mg; about 2-6 mg; about 3-7 mg; about 4-8 mg; about 5-10 mg; about 6-11 mg; about 7-12 mg; about 8-13 mg; about 9-11 mg; about 9-14 mg; about 10-15 mg; about 11-16 mg; about 12-17 mg; about 13-18 mg; about 14-19 mg; about 15-20 mg; about 5-15 mg; about 10-20 mg; about 0.5 mg; about 1 mg; about 1.5 mg; about 2 mg; about 2.5 mg; about 3 mg; about 3.5 mg; about 4 mg; about 4.5 mg; about 5 mg; about 6 mg; about 7 mg; about 7.5 mg; about 10 mg; about 15 mg; about 30 mg; or any amount in a range bounded by, or between, any of these values. These doses may be a safe dose for repeated administration, such as 1, 2, 3, or 4 times a day, or repeated at an interval of 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, about 4 weeks, about 4-6 weeks, about 1-2 months, about 6 weeks, about 2-3 months, about 3-4 months, about 4-5 months, about 5-6 months, about 6-7 months, about 7-8 months, about 8-9 months, about 9-10 months, about 10-11 months, about 11-12 months, about 2 years, etc.

For some dosage forms, the cyclodextrin (such as SBEβCD) may be present in an amount of about 1-200 mg; about 1-100 mg; 25-175 mg; about 50-150 mg; about 50-100 mg; about 50-200 mg; about 25-100 mg; about 75-150 mg; about 100-175 mg; about 20-80 mg; about 25-50 mg; about 60-100 mg; about 80-100 mg; about 100 mg; about 80-120 mg; about 100-120 mg; about 100-140 mg; about 120-160 mg; about 140-180 mg; about 150-200 mg, about 100-150 mg; about 30-90 mg; about 40-60 mg; about 40-80 mg; about 50-70 mg, about 55-65 mg, about 60-62 mg, or any amount in a range bounded by, or between, any of these values.

For some dosage forms, an inclusion complex of a drug (such as meloxicam or another NSAID, or rizatriptan, frovatriptan or another triptan) and cyclodextrin is about 1-10%, 5-20%, 5-15%, 6-16%, 7-17%, 8-18%, 9-19%, 10-20%, 15-30%, 30-40%, 40-50%, 50-70%, or 70-90% of the total weight of the dosage form, or any percentage in a range bounded by any of these values.

Some dosage forms contain a bicarbonate (e.g., sodium bicarbonate) in amount of about 1-2000 mg; about 1-1000 mg; about 100-1000 mg; about 200-800 mg; about 1-500 mg; about 1-200 mg; about 1-100 mg; about 50-750 mg; about 500-1000 mg; about 100-500 mg; about 100-300 mg; about 500-1000 mg; about 300-700 mg; about 400-600 mg; about 50-250 mg; about 50-100 mg; about 250-750 mg; about 100-200 mg; about 200-300 mg; about 300-400 mg;

about 400-500 mg; about 410-510 mg; about 420-520 mg; about 430-530 mg; about 440-540 mg; about 450-550 mg; about 460-560 mg; about 470-570 mg; about 480-580 mg; about 490-590 mg; about 500-600 mg; about 600-700 mg; about 700-800 mg; about 800-900 mg; about 900-1000 mg; about 150-650 mg; about 350-850 mg; about 400 mg; about 450 mg; about 500 mg, about 550 mg; about 600 mg; or any amount in a range bounded by, or between, any of these values.

A bicarbonate, such as sodium bicarbonate, may be at least about 10%, at least about 15%, at least about 20%, about 20-40%, about 30-50%, about 40-60%, about 50-70%, about 60-80%, or about 70-90%, or any percentage in a range bounded by any of these values, of the total weight of the dosage form.

In some embodiments, the daily dose of meloxicam, or the amount of meloxicam administered in a single day (either in one administration, or by more than one divided doses adding up to the daily dose) is about 2-5 mg, about 2-6 mg, about 2-7 mg, about 2-8 mg, about 2-9 mg, about 2-10 mg, about 2-11 mg, about 2-12 mg, about 2-13 mg, about 2-14 mg, about 2-15 mg, about 2-16 mg, about 2-17 mg, about 2-18 mg, about 2-19 mg, about 2-20 mg, about 2-21 mg, about 2-22 mg, about 2-23 mg, about 2-24 mg, about 2-25 mg, about 2-26 mg, about 2-27 mg, about 2-28 mg, about 2-29 mg, about 2-30 mg, about 2-35 mg, about 2-40 mg, about 2-45 mg, about 2-50 mg, about 2-55 mg, about 2-60 mg, about 2-65 mg, about 2-70 mg, about 2-75 mg, about 3-8 mg, about 4-9 mg, about 5-10 mg, about 6-11 mg, about 7-12 mg, about 8-13 mg, about 9-14 mg, about 10-15 mg, about 11-16 mg, about 12-17 mg, about 13-18 mg, about 14-19 mg, about 15-20 mg, about 16-21 mg, about 17-22 mg, about 18-23 mg, about 19-24 mg, about 20-25 mg, about 21-26 mg, about 22-27 mg, about 23-28 mg, about 24-29 mg, about 25-30 mg, about 26-31 mg, about 27-32 mg, about 28-33 mg, about 29-34 mg, about 30-35 mg, about 31-36 mg, about 32-37 mg, about 33-38 mg, about 34-39 mg, about 35-40 mg, about 36-41 mg, about 37-42 mg, about 38-43 mg, about 39-44 mg, about 40-45 mg, about 41-46 mg, about 42-47 mg, about 43-48 mg, about 44-49 mg, about 45-50 mg, about 46-51 mg, about 47-52 mg, about 48-53 mg, about 49-54 mg, about 50-55 mg, about 51-56 mg, about 52-57 mg, about 53-58 mg, about 54-59 mg, about 55-60 mg, about 56-61 mg, about 57-62 mg, about 58-63 mg, about 59-64 mg, about 60-65 mg, about 61-66 mg, about 62-67 mg, about 63-68 mg, about 64-69 mg, about 65-70 mg, about 66-71 mg, about 67-72 mg, about 68-73 mg, about 69-74 mg, about 70-75 mg, about 5-10 mg, about 10-15 mg, about 15-20 mg, about 20-25 mg, about 25-30 mg, about 30-35 mg, or any amount in a range bounded by any of these values. The daily dose may be given as a single dose, given once a day, or may be given in 2, 3, 4, or more divided doses during a day.

In some embodiments, the weekly dose of meloxicam or the amount of meloxicam administered in a week (either in one administration, or by more than one divided doses adding up to the weekly dose) is about 1-1000 mg; about 1-500 mg; about 10-250 mg; about 100-300 mg; about 10400 mg; about 10-150 mg; about 10-300 mg; about 20-150 mg; about 20-60 mg; about 30-70 mg; about 40-60 mg; about 50-70 mg; about 70-90 mg; about 90-110 mg; about 80-450 mg; about 80-100 mg; about 90-110 mg; about 100-120 mg; about 110-130 mg; about 120-140 mg; about 130-150 mg; about 140-160 mg; about 150-170 mg; about 160480 mg; about 170-190 mg; about 180-200 mg; about 190-210 mg; about 200-220 mg; about 210-230 mg; about 220-240 mg; about 230-250 mg; about 240-260 mg; about 250-270 mg; about 260-280 mg; about 270-290 mg; about 280-300 mg; about 290-310 mg; about 300-320 mg; about 310-330 mg; about 320-340 mg; about 330-350 mg; about 340-360 mg; about 350-370 mg; about 360-380 mg; about 370-390 mg; about 380-400 mg; about 390-410 mg; about 400-420 mg; about 410-430 mg; about 420-440 mg; about 430-450 mg; about 50 mg; about 55 mg; about 100-150 mg; about 30-100 mg; or any amount in a range bounded by, or between, any of these values. The weekly dose may be given as a single dose, given once a week, or may be given in 2, 3, 4, 5, 6, or 7 individual doses during a week.

In some embodiments, the monthly dose of meloxicam (e.g., an oral dose), or a dose administered over a period of a month, is about 5000 mg or less; about 4000 mg or less; about 3000 mg or less; about 2000 mg or less; about 1000 mg or less; about 700 mg or less; about 600 mg or less; about 300-2400 mg; about 300-350 mg; about 310-360 mg; about 320-370 mg; about 330-380 mg; about 340-390 mg; about 350-400 mg; about 360-410 mg; about 370-420 mg; about 380-430 mg; about 390-440 mg; about 400-450 mg; about 410-460 mg; about 420-470 mg; about 430-480 mg; about 440-490 mg; about 450-500 mg; about 460-510 mg; about 470-520 mg; about 480-530 mg; about 490-540 mg; about 500-550 mg; about 510-560 mg; about 520-570 mg; about 530-580 mg; about 540-590 mg; about 550-600 mg; about 560-610 mg; about 570-620 mg; about 580-630 mg; about 590-640 mg; about 600-650 mg; about 610-660 mg; about 620-670 mg; about 630-680 mg; about 640-690 mg; about 650-700 mg; about 660-710 mg; about 670-720 mg; about 680-730 mg; about 690-740 mg; about 700-750 mg; about 710-760 mg; about 720-770 mg; about 730-780 mg; about 740-790 mg; about 750-800 mg; about 760-810 mg; about 770-820 mg; about 780-830 mg; about 790-840 mg; about 800-850 mg; about 810-860 mg; about 820-870 mg; about 830-880 mg; about 840-890 mg; about 850-900 mg; about 860-910 mg; about 870-920 mg; about 880-930 mg; about 890-940 mg; about 900-950 mg; about 910-960 mg; about 920-970 mg; about 930-980 mg; about 940-990 mg; about 950-1000 mg; about 960-1010 mg; about 970-1020 mg; about 980-1030 mg; about 990-1040 mg; about 1000-1050 mg; about 1010-1060 mg; about 1020-1070 mg; about 1030-1080 mg; about 1040-1090 mg; about 1050-1100 mg; about 1060-1110 mg; about 1070-1120 mg; about 1080-1130 mg; about 1090-1140 mg; about 1100-1150 mg; about 1110-1160 mg; about 1120-1170 mg; about 1130-1180 mg; about 1140-1190 mg; about 1150-1200 mg; about 1160-1210 mg; about 1170-1220 mg; about 1180-1230 mg; about 1190-1240 mg; about 1200-1250 mg; about 1210-1260 mg; about 1220-1270 mg; about 1230-1280 mg; about 1240-1290 mg; about 1250-1300 mg; about 1260-1310 mg; about 1270-1320 mg; about 1280-1330 mg; about 1290-1340 mg; about 1300-1350 mg; about 1310-1360 mg; about 1320-1370 mg; about 1330-1380 mg; about 1340-1390 mg; about 1350-1400 mg; about 1360-1410 mg; about 1370-1420 mg; about 1380-1430 mg; about 1390-1440 mg; about 1400-1450 mg; about 1410-1460 mg; about 1420-1470 mg; about 1430-1480 mg; about 1440-1490 mg; about 1450-1500 mg; about 1460-1510 mg; about 1470-1520 mg; about 1480-1530 mg; about 1490-1540 mg; about 1500-1550 mg; about 1510-1560 mg; about 1520-1570 mg; about 1530-1580 mg; about 1540-1590 mg; about 1550-1600 mg; about 1560-1610 mg; about 1570-1620 mg; about 1580-1630 mg; about 1590-1640 mg; about 1600-1650 mg; about 1610-1660 mg; about 1620-1670 mg; about 1630-1680 mg; about 1640-1690 mg; about 1650-1700 mg; about 1660-1710 mg; about 1670-1720 mg; about 1680-1730 mg; about 1690-1740 mg; about 1700-1750 mg; about 1710-1760 mg; about 1720-1770 mg; about 1730-1780 mg; about 1740-1790 mg; about 1750-1800 mg; about 1760-1810 mg; about 1770-1820 mg; about 1780-1830 mg; about 1790-1840 mg; about 1800-1850 mg; about 1810-1860 mg; about 1820-1870 mg; about 1830-1880 mg; about 1840-1890 mg; about 1850-1900 mg; about 1860-1910 mg; about 1870-1920 mg; about 1880-1930 mg; about 1890-1940 mg; about 1900-1950 mg; about 1910-1960 mg; about 1920-1970 mg; about 1930-1980 mg; about 1940-1990 mg; about 1950-2000 mg; about 1960-2010 mg; about 1970-2020 mg; about 1980-2030 mg; about 1990-2040 mg; about 2000-2050 mg; about 2010-2060 mg; about 2020-2070 mg; about 2030-2080 mg; about 2040-2090 mg; about 2050-2100 mg; about 2060-2110 mg; about 2070-2120 mg; about 2080-2130 mg; about 2090-2140 mg; about 2100-2150 mg; about 2110-2160 mg; about 2120-2170 mg; about 2130-2180 mg; about 2140-2190 mg; about 2150-2200 mg; about 2160-2210 mg; about 2170-2220 mg; about 2180-2230 mg; about 2190-2240 mg; about 2200-2250 mg; about 2210-2260 mg; about 2220-2270 mg; about 2230-2280 mg; about 2240-2290 mg; about 2250-2300 mg; about 2260-2310 mg; about 2270-2320 mg; about 2280-2330 mg; about 2290-2340 mg; about 2300-2350 mg; about 2310-2360 mg; about 2320-2370 mg; about 2330-2380 mg; about 2340-2390 mg; about 2350-2400 mg; about 1-4000 mg; about 1-1000 mg; about 10-1000 mg; about 50-1000 mg; about 10-600 mg; about 40-600 mg; about 50-600 mg; about 40-400 mg; about 50-200 mg; about 200-240 mg; about 240-280 mg; about 280-320 mg; about 320-360 mg; about 360-400 mg; about 400-450 mg; about 450-500 mg; about 500-600 mg; about 250-350 mg; about 100-600 mg; about 40-2000 mg; about 40-800 mg; about 100-900 mg; about 100-800 mg; about 40-1000 mg; about 50-1000 mg; about 100-1000 mg; or any monthly dose in a range bounded by, or between, any of these values. A monthly dose may be given as a single dose, or as two or more individual doses administered during the month. In some embodiments, the monthly dose is administered bi-weekly in 2 or 3 divided doses. In some embodiments, the monthly dose is administered weekly in 4 or 5 divided doses. In some embodiments, the monthly dose is administered daily in 28 to 31 divided doses, or in 56 to 62 divided doses or more. In some embodiments, the monthly dose is administered in 5 to 15 individual doses during the month. The monthly dose may be administered for only 1 month, or may be repeatedly administered for 2, 3, 4, 5, 6, or more months.

In some embodiments, the daily dose of frovatriptan or another triptan (e.g., an oral dose, a parenteral dose, etc.) is about 0.5-1 mg, about 1-2 mg, about 2-3 mg, about 3-4 mg, about 2-5 mg, about 2-6 mg, about 2-7 mg, about 2-8 mg, about 2-9 mg, about 2-10 mg, about 2-11 mg, about 2-12 mg, about 2-13 mg, about 2-14 mg, about 2-15 mg, about 2-16 mg, about 2-17 mg, about 2-18 mg, about 2-19 mg, about 2-20 mg, about 2-21 mg, about 2-22 mg, about 2-23 mg, about 2-24 mg, about 2-25 mg, about 2-26 mg, about 2-27 mg, about 2-28 mg, about 2-29 mg, about 2-30 mg, about 2-35 mg, about 2-40 mg, about 5-10 mg, about 10-15 mg, about 15-20 mg, about 20-25 mg, about 25-30 mg, about 30-35 mg, or any amount in a range bounded by any of these values.

In some embodiments, the daily dose of rizatriptan is about 0.5-100 mg, about 5-50 mg, about 1-10 mg, about 10-20 mg, about 20-30 mg, about 30-40 mg, about 40-50 mg, about 1-5 mg, about 1-6 mg, about 2-7 mg, about 3-8 mg, about 4-9 mg, about 5-10 mg, about 6-11 mg, about 7-12 mg, about 8-13 mg, about 9-14 mg, about 10-15 mg, about 11-16 mg, about 12-17 mg, about 13-18 mg, about 14-19 mg, about 15-20 mg, about 16-21 mg, about 17-22 mg, about 18-23 mg, about 19-24 mg, about 20-25 mg, about 21-26 mg, about 22-27 mg, about 23-28 mg, about 24-29 mg, about 25-30 mg, about 26-31 mg, about 27-32 mg, about 28-33 mg, about 29-34 mg, about 30-35 mg, about 31-36 mg, about 32-37 mg, about 33-38 mg, about 34-39 mg, about 35-40 mg, about 36-41 mg, about 37-42 mg, about 38-43 mg, about 39-44 mg, about 40-45 mg, about 41-46 mg, about 42-47 mg, about 43-48 mg, about 44-49 mg, about 45-50 mg, about 46-51 mg, about 47-52 mg, the 48-53 mg, about 49-54 mg, about 50-55 mg, or any amount in a range bounded by any of these values. The daily dose may be given as a single dose, given once a day, or may be given in 2, 3, 4, or more divided doses during a day.

In some embodiments, the weekly dose of frovatriptan or another triptan (e.g., an oral dose) is about 1-1000 mg; about 1-500 mg; about 10-250 mg; about 100-300 mg; about 10-100 mg; about 10-150 mg; about 10-300 mg; about 20-150 mg; about 20-60 mg; about 30-70 mg; about 40-60 mg; about 50-70 mg; about 70-90 mg; about 90-110 mg; about 50 mg; about 55 mg; about 100450 mg; about 30-100 mg; about 1-20 mg; about 1-10 mg; about 2-10 mg; about 2-5 mg; about 5-10 mg; about 2.5 mg; about 5 mg; about 7.5 mg; or any amount in a range bounded by, or between, any of these values. The weekly dose may be given as a single dose, given once a week, or may be given in 2, 3, 4, 5, 6, or 7 individual doses during a week.

In some embodiments, the weekly dose of rizatriptan is about 1-1000 mg; about 10-400 mg, about 50-250 mg, about 1-500 mg; about 10-250 mg; about 100-300 mg; about 10-100 mg; about 10-150 mg; about 10-300 mg; about 20-150 mg; about 20-60 mg; about 30-70 mg; about 40-60 mg; about 50-70 mg; about 70-90 mg; about 90-110 mg; about 50 mg; about 55 mg; about 100-150 mg; about 30-100 mg; about 1-20 mg; about 140 mg; about 240 mg; about 2-5 mg; about 540 mg; about 1-50 mg; about 10-60 mg; about 20-70 mg; about 30-80 mg; how about 40-90 mg; about 50-100 mg; about 60-110 mg; about 70-120 mg; about 80-130 mg; about 90-140 mg; about 100-150 mg; about 110460 mg; about 120-170 mg; about 130-180 mg; about 140-190 mg; about 150-200 mg; about 160-210 mg; about 170-220 mg; about 180-230 mg; about 190-240 mg; about 200-250 mg; about 210-260 mg; about 220-270 mg; about 230-280 mg; about 240-290 mg; about 250-300 mg; about 260-310 mg; about 270-320 mg; about 280-330 mg; about 290-340 mg; about 300-350 mg; about 310-360 mg; about 320-370 mg; about 330-380 mg; about 340-390 mg; about 350-400 mg; or any amount in a range bounded by, or between, any of these values. The weekly dose may be given as a single dose, given once a week, or may be given in 2, 3, 4, 5, 6, or 7 individual doses during a week.

In some embodiments, the monthly dose of frovatriptan or another triptan (e.g., an oral dose), or a dose administered over a period of a month, is about 5000 mg or less; about 4000 mg or less; about 3000 mg or less; about 2000 mg or less; about 1000 mg or less; about 700 mg or less; about 600 mg or less; about 1-4000 mg; about 1-1000 mg; about 10-1000 mg; about 50-1000 mg; about 10-600 mg; about 40-600 mg; about 50-600 mg; about 40-400 mg; about 50-200 mg; about 200-240 mg; about 240-280 mg; about 280-320 mg; about 320-360 mg; about 360-400 mg; about 400-450 mg; about 450-500 mg; about 500-600 mg; about 250-350 mg; about 100-600 mg; about 40-2000 mg; about 40-800 mg; about 100-900 mg; about 100-800 mg; about 40-1000 mg; about 50-1000 mg; about 100-1000 mg; about 10-80 mg; about 10-40 mg; about 20-30 mg; or any monthly dose in a range bounded by, or between, any of these values. A monthly dose may be given as a single dose, or as two or more individual doses administered during the month. In some embodiments, the monthly dose is administered bi-weekly in 2 or 3 divided doses. In some embodiments, the monthly dose is administered weekly in 4 or 5 divided doses. In some embodiments, the monthly dose is administered daily in 28 to 31 divided doses, or in 56 to 62 divided doses or more. In some embodiments, the monthly dose is administered in 5 to 15 individual doses during the month. The monthly dose may be administered for only 1 month, or may be repeatedly administered for 2, 3, 4, 5, 6, or more months.

In some embodiments, the monthly dose of rizatriptan, or a total dose administered within a period of a month, is about 5000 mg or less; about 4000 mg or less; about 3000 mg or less; about 2000 mg or less; about 1000 mg or less; about 700 mg or less; about 600 mg or less; about 1-4000 mg; about 1-1000 mg; about 10-1000 mg; about 50-1000 mg; about 10-600 mg; about 40-600 mg; about 50-600 mg; about 150-2400 mg, about 150-200 mg; about 160-210 mg; about 170-220 mg; about 180-230 mg; about 190-240 mg; about 200-250 mg; about 210-260 mg; about 220-270 mg; about 230-280 mg; about 240-290 mg; about 250-300 mg; about 260-310 mg; about 270-320 mg; about 280-330 mg; about 290-340 mg; about 300-350 mg; about 310-360 mg; about 320-370 mg; about 330-380 mg; about 340-390 mg; about 350-400 mg; about 360-410 mg; about 370-420 mg; about 380-430 mg; about 390-440 mg; about 400-450 mg; about 410-460 mg; about 420-470 mg; about 430-480 mg; about 440-490 mg; about 450-500 mg; about 460-510 mg; about 470-520 mg; about 480-530 mg; about 490-540 mg; about 500-550 mg; about 510-560 mg; about 520-570 mg; about 530-580 mg; about 540-590 mg; about 550-600 mg; about 560-610 mg; about 570-620 mg; about 580-630 mg; about 590-640 mg; about 600-650 mg; about 610-660 mg; about 620-670 mg; about 630-680 mg; about 640-690 mg; about 650-700 mg; about 660-710 mg; about 670-720 mg; about 680-730 mg; about 690-740 mg; about 700-750 mg; about 710-760 mg; about 720-770 mg; about 730-780 mg; about 740-790 mg; about 750-800 mg; about 760-810 mg; about 770-820 mg; about 780-830 mg; about 790-840 mg; about 800-850 mg; about 810-860 mg; about 820-870 mg; about 830-880 mg; about 840-890 mg; about 850-900 mg; about 860-910 mg; about 870-920 mg; about 880-930 mg; about 890-940 mg; about 900-950 mg; about 910-960 mg; about 920-970 mg; about 930-980 mg; about 940-990 mg; about 950-1000 mg; about 960-1010 mg; about 970-1020 mg; about 980-1030 mg; about 990-1040 mg; about 1000-1050 mg; about 1010-1060 mg; about 1020-1070 mg; about 1030-1080 mg; about 1040-1090 mg; about 1050-1100 mg; about 1060-1110 mg; about 1070-1120 mg; about 1080-1130 mg; about 1090-1140 mg; about 1100-1150 mg; about 1110-1160 mg; about 1120-1170 mg; about 1130-1180 mg; about 1140-1190 mg; about 1150-1200 mg; about 1160-1210 mg; about 1170-1220 mg; about 1180-1230 mg; about 1190-1240 mg; about 1200-1250 mg; about 1210-1260 mg; about 1220-1270 mg; about 1230-1280 mg; about 1240-1290 mg; about 1250-1300 mg; about 1260-1310 mg; about 1270-1320 mg; about 1280-1330 mg; about 1290-1340 mg; about 1300-1350 mg; about 1310-1360 mg; about 1320-1370 mg; about 1330-1380 mg; about 1340-1390 mg; about 1350-1400 mg; about 1360-1410 mg; about 1370-1420 mg; about 1380-1430 mg; about 1390-1440 mg; about 1400-1450 mg; about 1410-1460 mg; about 1420-1470 mg; about 1430-1480 mg; about 1440-1490 mg; about 1450-1500 mg; about 1460-1510 mg; about 1470-1520 mg; about 1480-1530 mg; about 1490-1540 mg; about 1500-1550 mg; about 1510-1560 mg; about 1520-1570 mg; about 1530-1580 mg; about 1540-1590 mg; about 1550-1600 mg; about 1560-1610 mg; about 1570-1620 mg; about 1580-1630 mg; about 1590-1640 mg; about 1600-1650 mg; about 1610-1660 mg; about 1620-1670 mg; about 1630-1680 mg; about 1640-1690 mg; about 1650-1700 mg; about 1660-1710 mg; about 1670-1720 mg; about 1680-1730 mg; about 1690-1740 mg; about 1700-1750 mg; about 1710-1760 mg; about 1720-1770 mg; about 1730-1780 mg; about 1740-1790 mg; about 1750-1800 mg; about 1760-1810 mg; about 1770-1820 mg; about 1780-1830 mg; about 1790-1840 mg; about 1800-1850 mg; about 1810-1860 mg; about 1820-1870 mg; about 1830-1880 mg; about 1840-1890 mg; about 1850-1900 mg; about 1860-1910 mg; about 1870-1920 mg; about 1880-1930 mg; about 1890-1940 mg; about 1900-1950 mg; about 1910-1960 mg; about 1920-1970 mg; about 1930-1980 mg; about 1940-1990 mg; about 1950-2000 mg; about 1960-2010 mg; about 1970-2020 mg; about 1980-2030 mg; about 1990-2040 mg; about 2000-2050 mg; about 2010-2060 mg; about 2020-2070 mg; about 2030-2080 mg; about 2040-2090 mg; about 2050-2100 mg; about 2060-2110 mg; about 2070-2120 mg; about 2080-2130 mg; about 2090-2140 mg; about 2100-2150 mg; about 2110-2160 mg; about 2120-2170 mg; about 2130-2180 mg; about 2140-2190 mg; about 2150-2200 mg; about 2160-2210 mg; about 2170-2220 mg; about 2180-2230 mg; about 2190-2240 mg; about 2200-2250 mg; about 2210-2260 mg; about 2220-2270 mg; about 2230-2280 mg; about 2240-2290 mg; about 2250-2300 mg; about 2260-2310 mg; about 2270-2320 mg; about 2280-2330 mg; about 2290-2340 mg; about 2300-2350 mg; about 2310-2360 mg; about 2320-2370 mg; about 2330-2380 mg; about 2340-2390 mg; about 2350-2400 mg; about 40-400 mg; about 50-200 mg; about 200-240 mg; about 240-280 mg; about 280-320 mg; about 320-360 mg; about 360-400 mg; about 400-450 mg; about 450-500 mg; about 500-600 mg; about 250-350 mg; about 100-600 mg; about 40-2000 mg; about 40-800 mg; about 100-900 mg; about 100-800 mg; about 40-1000 mg; about 50-1000 mg; about 100-1000 mg; about 10-80 mg; about 10-40 mg; about 20-30 mg; or any monthly dose in a range bounded by, or between, any of these values. A monthly dose may be given as a single dose, or as two or more individual doses administered during the month. In some embodiments, the monthly dose is administered bi-weekly in 2 or 3 divided doses. In some embodiments, the monthly dose is administered weekly in 4 or 5 divided doses. In some embodiments, the monthly dose is administered daily in 28 to 31 divided doses, or in 56 to 62 divided doses or more. In some embodiments, the monthly dose is administered in 5 to 15 individual doses during the month. The monthly dose may be administered for only 1 month, or may be repeatedly administered for 2, 3, 4, 5, 6, or more months.

In other embodiments, the dosage form may be administered weekly for about one, two, three, four, or more consecutive weeks, every other week or bi-weekly, or once every three weeks. This regimen may be repeated once weekly, twice in a month, three times in a month, once monthly, once every two months, once every three months, or as directed by a medical professional.

In certain embodiments, administering the pharmaceutical composition results in improvement of pharmacokinetics, for example in fasted human subjects, such as increased bioavailability (e.g., reduced $T_{max}$, increased $C_{max}$, increased AUC, etc.) of a drug, such as meloxicam or another NSAID, rizatriptan, frovatriptan, or another triptan, in the dosage form as compared to a dosage form containing the drug but not containing a cyclodextrin, an acid inhibitor, or a buffering agent (such as a bicarbonate). In some embodiments, the bioavailability of the drug will increase with repeated dosing. For example, the bioavailability of the drug (such as meloxicam or another NSAID, rizatriptan, frovatriptan, or another triptan) in the dosage form, for example in fasted human subjects, may increase after about 1-10 days of repeated dosing; about 2-6 days of repeated dosing; about 3-5 days of repeated dosing; about 4-6 days of repeated dosing; about 5-8 days of repeated dosing; about 5 days of repeated dosing; about 6 days of repeated dosing; about 7 days of repeated dosing; about 8 days of repeated dosing; about 10 days of repeated dosing; about 15 days of repeated dosing; or time period in any range bounded by, or between, any of these values; as compared to the bioavailability of the drug in a dosage form not containing a cyclodextrin, an acid inhibitor, or a buffering agent (such as a bicarbonate). Administering a drug in any dosage forms described herein to a human subject or patient may improve or achieve the desired oral pharmacokinetic properties of the drug.

Any reference to $T_{max}$, $C_{max}$, AUC, or any other pharmacokinetic parameter should be understood to include an average, mean, or median value in human beings, such as human patients or human subjects.

Administering some of the dosage forms to a human being may result in a desired range for an area under the plasma concentration curve (AUC) of meloxicam. For example the dosage forms with meloxicam may result in an AUC of meloxicam, such as a median, mean, or average AUC of meloxicam in human beings, of about 1-150 µg·hr/mL; about 10-30 µg·hr/mL; about 20-40 µg·hr/mL; about 30-50 µg·hr/mL; about 40-60 µg·hr/mL; about 50-70 µg·hr/mL; about 60-80 µg·hr/mL; about 70-90 µg·hr/mL; about 80-100 µg·hr/mL; about 10-100 µg·hr/mL; about 50-150 µg·hr/mL; about 25-125 µg·hr/mL; about 75-150 µg·hr/mL; about 20-50 µg·hr/mL; about 40-70 µg·hr/mL; about 60-90 µg·hr/mL; about 80-110 µg·hr/mL; about 100-130 µg·hr/mL; about 120-150 µg·hr/mL; about 100-150 µg·hr/mL; or any AUC in a range bounded by, or between, any of these values.

Administering some of the dosage forms to a human being may result in a desired range for an area under the plasma concentration curve (AUC) of frovatriptan. For example the dosage forms with frovatriptan or another triptan may result in an AUC of frovatriptan, such as a median, mean, or average AUC of frovatriptan in human beings, or another triptan of about 1-150 µg·hr/mL; about 10-30 µg·hr/mL; about 20-40 µg·hr/mL; about 30-50 µg·hr/mL; about 40-60 µg·hr/mL; about 50-70 µg·hr/mL; about 60-80 µg·hr/mL; about 70-90 µg·hr/mL; about 80-100 µg·hr/mL; about 10-100 µg·hr/mL; about 50-150 µg·hr/mL; about 25-125 µg·hr/mL; about 75-150 µg·hr/mL; about 20-50 µg·hr/mL; about 40-70 µg·hr/mL; about 60-90 µg·hr/mL; about 80-110 µg·hr/mL; about 100-130 µg·hr/mL; about 120-150 µg·hr/mL; or any AUC in a range bounded by, or between, any of these values.

Unless otherwise indicated, the AUC refers to the AUC calculated to the last measured concentration ($AUC_{0-t}$), over a period of 24 hours ($AUC_{0-24}$), or extrapolated to infinity ($AUC_{0-inf}$).

For some acute pain conditions, such as migraine and other types of headache, the AUC for a short period after oral administration, such as an AUC measured over 6 hours (or $AUC_{0-6}$), may be of particular interest, e.g. for quick pain relief. For example, some dosage forms may result in an $AUC_{0-6}$ of meloxicam, such as a median, mean, or average $AUC_{0-6}$ of meloxicam in human beings, that is at least about 6 µg·hr/mL (or 6,000 ng·hr/mL); at least about 7 µg·hr/mL (or 7,000 ng·hr/mL); at least about 8 µg·hr/mL (or 8,000 ng·hr/mL); at least about 9 µg·hr/mL (or 9,000 ng·hr/mL); about 6-10 µg·hr/mL; about 7-11 µg·hr/mL; about 8-12 µg·hr/mL; about 9-13 µg·hr/mL; or any $AUC_{0-6}$ in a range bounded by, or between, any of these values.

In some embodiments, the dosage form may result in a $C_{max}$ of meloxicam, such as a median, mean, or average $C_{max}$ of meloxicam in human beings, of about 10-2500 ng/mL; about 100-2250 ng/mL; about 500-2000 ng/mL; about 1000-2500 ng/mL; about 1000-2000 ng/mL; about 100-900 ng/mL; about 750-1500 ng/mL; about 1250-2000 ng/mL; about 1500-2300 ng/mL; about 800-1200 ng/mL; about 1900-2400 ng/mL; about 50-500 ng/mL; about 400-950 ng/mL; about 900-1500 ng/mL; about 1100-2200 ng/mL; about 1300-1600 ng/mL; about 1200-1500 ng/mL; about 1400-2100 ng/mL; about 1500-1900 ng/mL; about 1600-2100 ng/mL; about 1700-2000 ng/mL; about 1900-2500 ng/mL; about 1500-1700 ng/mL; about 1600-1800 ng/mL; about 1700-1900 ng/mL; about 1800-2000 ng/mL; about 1900-2100 ng/mL; about 2000-2200 ng/mL; about 2100-2300 ng/mL; about 2200-2400 ng/mL; about 2300-2500 ng/mL; about 2500-3000 ng/mL; at least about 1400 ng/mL; at least about 1500 ng/mL; at least about 1600 ng/mL; at least about 1700 ng/mL; at least about 1800 ng/mL; at least about 1900 ng/mL; at least about 2000 ng/mL; at least about 2100 ng/mL; at least about 2200 ng/mL; at least about 2300 ng/mL; at least about 2400 ng/mL; at least about 2500 ng/mL; or any $C_{max}$ in a range bounded by, or between, any of these values.

In some embodiments, the dosage form may result in a $C_{max}$ of frovatriptan, such as a median, mean, or average $C_{max}$ of frovatriptan in human beings, of about 10-2500 ng/mL; about 100-2250 ng/mL; about 500-2000 ng/mL; about 1000-2500 ng/mL; about 1000-2000 ng/mL; about 100-900 ng/mL; about 750-1500 ng/mL; about 1250-2000 ng/mL; about 1500-2300 ng/mL; about 800-1200 ng/mL; about 1900-2400 ng/mL; about 50-500 ng/mL; about 400-950 ng/mL; about 900-1500 ng/mL; about 1100-2200 ng/mL; about 1300-1600 ng/mL; about 1200-1500 ng/mL; about 1400-2100 ng/mL; about 1500-1900 ng/mL; about 1600-2100 ng/mL; about 1700-2000 ng/mL; about 1900-2500 ng/mL; about 150-1700 ng/mL; about 1600-1800 ng/mL; about 1700-1900 ng/mL; about 1800-2000 ng/mL; about 1900-2100 ng/mL; about 2000-2200 ng/mL; about 2100-2300 ng/mL; about 2200-2400 ng/mL; about 2300-2500 ng/mL; about 2500-3000 ng/mL; or any $C_{max}$ in a range bounded by, or between, any of these values.

For example, a method described herein may reduce the $T_{max}$ of meloxicam, such as a median, mean, or average $T_{max}$ of meloxicam in human beings. In some embodiments, the method may include treating a patient to achieve the $T_{max}$ of meloxicam in the patient within about 10 minutes; within about 20 minutes; within about 30 minutes; within about 40 minutes; within about 50 minutes; within about 60 minutes; within about 70 minutes; within about 80 minutes; within about 90 minutes; within about 100 minutes; within about 110 minutes; within about 120 minutes; within about 180 minutes; about 10-30 minutes; about 20-40 minutes, about 30-50 minutes, about 40-60 minutes; about 50-70 minutes; about 60-90 minutes; about 70-100 minutes; about 80-110 minutes; about 90-120 minutes; about 1-10 hr; about 2-9 hr; about 3-7 hr; about 4-6 hr; about 1-5 hr; about 2-7 hr; about 3-8 hr; about 4-9 hr; about 1-4 hr; about 2-5 hr; about 3-6 hr; about 4-7 hr; about 5-8 hr; about 6-9 hr; about 7-10 hr; or any $T_{max}$ in a range bounded by, or between, any of these values; after administration of the dosage forms described above.

In some embodiments, an oral dosage form may have a $T_{max}$ of meloxicam, such as a median, mean, or average $T_{max}$ of meloxicam in human being, that is shorter than would be achieved by administering meloxicam by intramuscular injection. In some embodiments, an oral dosage form may have a $T_{max}$ of meloxicam that is shorter, or may increase meloxicam plasma levels at a faster rate, by a factor of at least about 1.5, about 2, about 3, about 4, about 5, about 6, about 7, about 8, about 9, about 10, about 12, about 15, about 20, or by a factor of about 1.1-2, about 1.5-3, about 2-4, about 3-5, about 4-6, about 1.5-1000, about 2-100, about 3-100, about 4-100, about 5-100, about 6-100, about 7-100, about 8-100, about 9-100, about 10-100, about 12-100, about 15-100, about 20-100, or by a factor in a range bounded by any of these values, as compared to that observed by intramuscular injection.

In some embodiments, an oral dosage form may have a time to half-maximal plasma concentration of meloxicam, such as a median, mean, or average time to half-maximal plasma concentration in human beings, that is less than about 5 minutes; less than about 10 minutes; less than about 15 minutes; less than about 20 minutes; less than about 25 minutes; less than about 30 minutes; less than about 35 minutes; less than about 40 minutes; less than about 45 minutes; less than about 50 minutes; less than about 55 minutes; less than about 60 minutes; less than about 90 minutes; about 5-15 minutes; about 10-20 minutes, about 15-25 minutes, about 20-30 minutes; about 25-35 minutes; about 30-45 minutes; about 35-50 minutes; about 40-55 minutes; about 45-60 minutes; about 0.5-5 hours; or any time in a range bounded by any of these values.

For example, a method described herein may reduce the $T_{max}$ of frovatriptan, such as a median, mean, or average $T_{max}$ of frovatriptan in human beings. In some embodiments, the method may include treating a patient to achieve the $T_{max}$ of frovatriptan in the patient within about 10 minutes; about 20 minutes; about 30 minutes; about 40 minutes; about 50 minutes; about 60 minutes; about 70 minutes; about 80 minutes; about 90 minutes; about 100 minutes; about 110 minutes; about 120 minutes; about 180 minutes; about 10-30 minutes; about 20-40 minutes; about 30-50 minutes; about 40-60 minutes; about 50-70 minutes; about 60-80 minutes; about 70-90 minutes; about 0.1-1 hour; about 0.1-0.5 hour; about 0.5-1 hour; about 1-10 hr; about 2-9 hr; about 3-7 hr; about 4-6 hr; about 1-5 hr; about 2-7 hr; about 3-8 hr; about 4-9 hr; about 1-4 hr; about 2-5 hr; about 3-6 hr; about 4-7 hr; about 5-8 hr; about 6-9 hr; about 7-10 hr; after administration or any $T_{max}$ in a range bounded by, or between, any of these values.

In some embodiments, a dosage form comprising meloxicam may result in a plasma concentration of meloxicam, such as a median, mean, or average plasma concentration of meloxicam in human beings, at 12 hours that is about 0.01-0.5 µg/mL; about 0.5-0.7 µg/mL; about 0.6-0.8 µg/mL; about 0.7-0.9 µg/mL; about 0.8-1 µg/mL; about 0.01-1 µg/mL; about 0.9-1.1 µg/mL; about 1-1.2 µg/mL; about 1.1-1.3 µg/mL; about 1.2-1.4 µg/mL; about 1.3-1.5 µg/mL; about 1-1.5 µg/mL; about 1.4-1.6 µg/mL; about 1.5-1.7 µg/mL; about 1.6-1.8 µg/mL; about 1.7-1.9 µg/mL; about 1.8-2 µg/mL; about 1.5-2 µg/mL; about 1.9-2.1 µg/mL; about 2-2.2 µg/mL; about 2.1-2.3 µg/mL; about 2.2-2.4 µg/mL; about 2.3-2.5 µg/mL; about 2-2.5 µg/mL; about 2.4-2.6 µg/mL; about 2.5-2.7 µg/mL; about 2.6-2.8 µg/mL; about 2.7-2.9 µg/mL; about 2.8-3 µg/mL; about 2.5-3 µg/mL; about 2.9-3.1 µg/mL; about 3-3.2 µg/mL; about 3.1-3.3 µg/mL; about 3.2-3.4 µg/mL; about 3.3-3.5 µg/mL; about 3.4-3.5 µg/mL; about 3.4-3.6 µg/mL; about 3.5-3.7 µg/mL; about 3.6-3.8 µg/mL; about 3.7-3.9 µg/mL; about 3.8-4 µg/mL; about 3.5-4 µg/mL; or any plasma concentration of meloxicam at 12 hours in a range bounded by, or between, any of these values.

In some embodiments, meloxicam is administered at a dose that results in a meloxicam average plasma level (such as a $C_{ave}$, or average plasma level) of about 0.01-0.5 µg/mL; about 0.5-0.7 µg/mL; about 0.6-0.8 µg/mL; about 0.7-0.9 µg/mL; about 0.8-1 µg/mL; about 0.01-1 µg/mL; about 0.9-1.1 µg/mL; about 1-1.2 µg/mL; about 1.1-1.3 µg/mL; about 1.2-1.4 µg/mL; about 1.3-1.5 µg/mL; about 1.4-1.6 µg/mL; about 1.5-1.7 µg/mL; about 1.6-1.8 µg/mL; about 1.7-1.9 µg/mL; about 1.8-2 µg/mL; about 1-2 µg/mL; about 0.01-3 µg/mL; about 1.9-2.1 µg/mL; about 2-2.2 µg/mL; about 2.1-2.3 µg/mL; about 2.2-2.4 µg/mL; about 2.3-2.5 µg/mL; about 2.4-2.6 µg/mL; about 2.5-2.7 µg/mL; about 2.6-2.8 µg/mL; about 2.7-2.9 µg/mL; about 2.8-3 µg/mL; about 2-3 µg/mL; about 2.9-3.1 µg/mL; about 3-3.2 µg/mL; about 3.1-3.3 µg/mL; about 3.2-3.4 µg/mL; about 3.3-3.5 µg/mL; about 3.4-3.6 µg/mL; about 3.5-3.7 µg/mL; about 3.6-3.8 µg/mL; about 3.7-3.9 µg/mL; about 3.8-4 µg/mL; about 3-4 µg/mL; about 2-4 µg/mL; about 0.01-4 µg/mL; about 0.1-20 µg/mL; about 0.5-15 µg/mL; about 0.5-10 µg/mL; about 5-15 µg/mL; about 10-20 µg/mL; about 7.5-15 µg/mL; about 2-10 µg/mL; about 1-8 µg/mL; about 1-6 µg/mL; about 1-2 µg/mL; about 0.5-3.5 µg/mL; about 0.5-7 µg/mL; about 12-20 µg/mL; about 8-12 µg/mL; about 1-4 µg/mL; about 4-7 µg/mL; about 7-11 µg/mL; about 11-15 µg/mL; about 15-19 µg/mL; about 16-20 µg/mL; or any meloxicam average plasma level in a range bounded by, or between, any of these values.

In some embodiments, a dosage form comprising frovatriptan may result in a plasma concentration of frovatriptan at 12 hours that is about 0.01-0.5 µg/mL; about 0.5-0.7 µg/mL; about 0.6-0.8 µg/mL; about 0.7-0.9 µg/mL; about 0.8-1 µg/mL; about 0.9-1.1 µg/mL; about 1-1.2 µg/mL; about 1.1-1.3 µg/mL; about 1.2-1.4 µg/mL; about 1.3-1.5 µg/mL; about 1.4-1.6 µg/mL; about 1.5-1.7 µg/mL; about 1.6-1.8 µg/mL; about 1.7-1.9 µg/mL; about 1.8-2 µg/mL; about 1.9-2.1 µg/mL; about 2-2.2 µg/mL; about 2.1-2.3 µg/mL; about 2.2-2.4 µg/mL; about 2.3-2.5 µg/mL; about 2.4-2.6 µg/mL; about 2.5-2.7 µg/mL; about 2.6-2.8 µg/mL; about 2.7-2.9 µg/mL; about 2.8-3 µg/mL; about 2.9-3.1 µg/mL; about 3-3.2 µg/mL; about 3.1-3.3 µg/mL; about 3.2-3.4 µg/mL; about 3.3-3.5 µg/mL; about 3.4-3.6 µg/mL; about 3.5-3.7 µg/mL; about 3.6-3.8 µg/mL; about 3.7-3.9 µg/mL; about 3.8-4 µg/mL; or any plasma concentration of frovatriptan at 12 hours in a range bounded by, or between, any of these values.

In some embodiments, frovatriptan is administered at a dose that results in an average frovatriptan plasma level (such as a $C_{ave}$, or average plasma level) of about 0.01-0.5 µg/mL; about 0.5-0.7 µg/mL; about 0.6-0.8 µg/mL; about 0.7-0.9 µg/mL; about 0.8-1 µg/mL; about 0.9-1.1 µg/mL; about 1-1.2 µg/mL; about 1.1-1.3 µg/mL; about 1.2-1.4 µg/mL; about 1.3-1.5 µg/mL; about 1.4-1.6 µg/mL; about 1.5-1.7 µg/mL; about 1.6-1.8 µg/mL; about 1.7-1.9 µg/mL; about 1.8-2 µg/mL; about 1.9-2.1 µg/mL; about 2-2.2 µg/mL; about 2.1-2.3 µg/mL; about 2.2-2.4 µg/mL; about 2.3-2.5 µg/mL; about 2.4-2.6 µg/mL; about 2.5-2.7 µg/mL; about 2.6-2.8 µg/mL; about 2.7-2.9 µg/mL; about 2.8-3 µg/mL; about 2.9-3.1 µg/mL; about 3-3.2 µg/mL; about 3.1-3.3 µg/mL; about 3.2-3.4 µg/mL; about 3.3-3.5 µg/mL; about 3.4-3.6 µg/mL; about 3.5-3.7 µg/mL; about 3.6-3.8 µg/mL; about 3.7-3.9 µg/mL; about 3.8-4 µg/mL; about 0.1-20 µg/mL; about 0.5-15 µg/mL; about 0.5-10 µg/mL; about 5-15 µg/mL; about 10-20 µg/mL; about 7.5-15 µg/mL; about 2-10 µg/mL; about 1-8 µg/mL; about 1-6 µg/mL; about 1-2 µg/mL; about 0.5-3.5 µg/mL; about 0.5-7 µg/mL;

about 12-20 µg/mL; about 8-12 µg/mL; about 1-4 µg/mL; about 4-7 µg/mL; about 7-11 µg/mL; about 11-15 µg/mL; about 15-19 µg/mL; about 16-20 µg/mL; or any amount of frovatriptan average plasma level in a range bounded by, or between, any of these values.

In some embodiments, the dosage form may be formulated for oral administration, for example, with an inert diluent or with an edible carrier, or it may be enclosed in hard or soft shell gelatin capsules, compressed into tablets, or incorporated directly with the food of the diet. For oral therapeutic administration, the active compound may be incorporated with an excipient and used in the form of ingestible tablets, buccal tablets, coated tablets, troches, capsules, elixirs, dispersions, suspensions, solutions, syrups, wafers, patches, and the like.

Tablets, troches, pills, capsules and the like may also contain one or more of the following: a binder such as gum tragacanth, acacia, corn starch or gelatin; an excipient, such as dicalcium phosphate; a disintegrating agent such as corn starch, potato starch, alginic acid and the like; a lubricant such as magnesium stearate; a sweetening agent such as sucrose, lactose or saccharin; or a flavoring agent such as peppermint, oil of wintergreen or cherry flavoring. When the unit dosage form is a capsule, it may contain, in addition to materials of the above type, a liquid carrier. Various other materials may be present as coating, for instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. It may be desirable for material in a dosage form or pharmaceutical composition to be pharmaceutically pure and substantially non-toxic in the amounts employed.

Some compositions or dosage forms may be a liquid, or may comprise a solid phase dispersed in a liquid.

The dosage form may further comprise an additional therapeutically active agents, such as an acid inhibitor or an analgesic.

In some embodiments, the dosage form may further comprise an acid inhibitor present in an amount effective to raise the gastric pH of a patient to at least 2, to at least 2.5, to at least 3, to at least 3.5, to at least 4, and more to at least 5, when one or more unit dosage forms are administered. The term "acid inhibitor" refers to agents that inhibit gastric acid secretion and increase gastric pH. Specific $H_2$ blockers, also referred to as $H_2$ antagonists or histamine $H_2$ blockers or antagonists, which may be used include but are not limited to cimetidine, ranitidine, ebrotidine, pabutidine, lafutidine, loxtidine, famotidine, or combinations thereof.

Other agents that may be effectively used as acid inhibitors are the proton pump inhibitors such as omeprazole, esomeprazole, pantoprazole, lansoprazole, dexlansoprazole, rabeprazole, pariprazole, leminoprazole and tenatoprazole. In some embodiments the daily dose of the acid inhibitor, such as esomeprazole, is about 1-200 mg, about 1-100 mg, about 50-100 mg, about 1-50 mg, about 40-80 mg, about 5-50 mg, about 20-40 mg, about 10-50 mg, about 10-20 mg, about 20-40 mg, about 15-50 mg, about 30-60 mg, about 10 mg, about 20 mg, about 30 mg, about 40 mg or any other amount in a range bounded by, or between, any of these values.

Examples of particular proton pump inhibitors include esomeprazole, present in unit dosage forms in an amount of between 5 mg and 50 mg; omeprazole, present in unit dosage forms in an amount of between 5 mg and 50 mg; lansoprazole, present in unit dosage forms in an amount of between 5 mg and 150 mg (and preferably at between 5 mg and 30 mg); and pantoprazole, present in unit dosage forms in an amount of between 10 mg and 200 mg. In some embodiments, the proton pump inhibitor (such as esomeprazole) is present in the dosage form in an amount of about 10-30 mg, about 20-40 mg, about 30-50 mg, about 40-60 mg, about 50-70 mg, about 60-80 mg, about 70-90 mg, or about 80-100 mg. Recently, a newer class of acid inhibitor has been developed which competes with potassium at the acid pump. The compounds in this class have been referred to as "reversible proton pump inhibitors" or "acid pump antagonists" and may also be used. Examples include AZD-0865, AR-H047108, CS-526, pumaprazole, revaprazan and soraprazan (see WO9605177 and WO9605199). Other compounds in this group are H-335/25 (AstraZeneca, Dialog file 128, accession number 020806); Sch-28080 (Schering Plough, Dialog file 128, accession number 009663); Sch-32651 (Schering Plough, Dialog file 128, accession number 006883) and SK&F-96067 (CAS Registry no. 115607-61-9).

Additional therapeutically active agents may include an analgesic such as a second non-steroidal anti-inflammatory drug, an opioid, a steroid, a triptan, etc. In some embodiments, the dosage form or treatment also further comprises administering a second non-steroidal anti-inflammatory drug in an amount effective to reduce or eliminate pain or inflammation. It will be understood that, for the purposes of the present disclosure, reference to an acid inhibitor, NSAID, or analgesic agent will include all of the common forms of these compounds and, in particular, their pharmaceutically acceptable salts. The amounts of NSAIDs which are therapeutically effective may be lower in the current embodiments than otherwise found in practice due to potential positive kinetic interaction and NSAID absorption in the presence of an acid inhibitor, and or in the presence of a buffering agent.

In other embodiments, the dosage form or treatment may further comprise administering an opioid in an amount effective to reduce or eliminate pain or inflammation. The opioid may include, but is not limited to, (dextro)propoxyphene, A-methylfentanyl, alfentanil, allylprodine, bezitramide, buprenorphine, butorphanol, carfentanyl, desmethylprodine, dextromoramide, dezocine, diacetylmorphine, dihydrocodeinone, dihydroetorphine, dimorphone, diphenoxylate, dipipanone, etorphine, fentanyl, ketobemidone, lefetamine, levacetylmethadol, levomethorphan, levorphanol, loperamide, meperidine, meptazinol, methadone, methylmorphine, morphine, nalbuphine, nalmefene, naloxone, naltrexone, nicomorphine, ohmefentanyl, oripavine, oxycodone, oxymorphone, PEPAP, paramorphine, pentazocine, phenazocine, piritramide, prodine, remifentanil, sufentanil, tapentadol, tilidine, tramadol, or combinations thereof.

The term "unit dosage form" as used herein refers to a single entity for drug administration. For example, a single tablet or capsule combining both a triptan and an NSAID would be a unit dosage form. A "unit dosage form" (or "unit dose form") may also be referred to as a "fixed dosage form" (or "fixed dose form") or "fixed dosage combination" (or "fixed dose combination") and are otherwise interchangeable. In one embodiment, the unit dosage form is a multilayer tablet.

In another embodiment, the unit dosage form is suitable for oral administration to a patient. In yet another embodiment, the unit dosage form is a tablet. In still another embodiment, the unit dosage form is a multilayer tablet comprising a single core and one or more layers outside of the core. In some embodiments, the pharmaceutical composition may have an effective amount of a triptan (such as rizatriptan or frovatriptan), a cyclodextrin, and a bicarbonate to increase bioavailability of rizatriptan or frovatriptan. In other embodiments, the pharmaceutical composition may have an effective amount of the triptan, sulfobutylether-β-cyclodextrin (SBEβCD), and sodium bicarbonate to increase bioavailability of the triptan or reduce the $T_{max}$ of the triptan.

Some dosage forms may comprise a first layer comprising meloxicam, an SBEβCD, and a bicarbonate; and a second layer comprising a triptan and a bicarbonate.

The first layer may contain, for example, any amount of meloxicam in one of the ranges recited above. For example, all of the meloxicam in the dosage form may be present in the first layer. The second layer may contain all of triptan, such that any amount in the ranges recited above with respect to the triptan may apply to the second layer.

In some embodiments, the first layer contains about 10-200 mg, about 50-150 mg, about 50-100 mg, about 70-120 mg, about 90-140 mg, or about 100 mg of the bicarbonate, such as sodium bicarbonate, or any amount of the bicarbonate in a range bounded by any of these values.

In some embodiments, the second layer contains about 100-500 mg, about 200-500 mg, about 300-500 mg, about 350-450 mg, about 380-420 mg, or about 400 mg of the bicarbonate, such as sodium bicarbonate, or any amount of the bicarbonate in a range bounded by any of these values.

Some oral dosage forms may have enteric coatings or film coatings. In some embodiments, a dosage form may comprise a tablet or a capsule having an enteric coating. In some embodiments, a dosage form may comprise a tablet or a capsule having a film coating.

An embodiment of the present disclosure is directed to a pharmaceutical composition in unit dosage form suitable for administration to a patient, comprising:

(a) dexketoprofen, which may or may not be surrounded by an enteric coating;

(b) sodium or potassium bicarbonate and/or sodium or potassium carbonate; and (c) frovatriptan, which may or may not be formulated with a cyclodextrin, and which may or may not be surrounded by an enteric coating In certain embodiments, the pharmaceutical composition results in faster release or dissolution of a drug (e.g. meloxicam or another NSAID, rizatriptan, frovatriptan, or another triptan) from the dosage form as compared to a dosage form containing the same drug but not containing the acid inhibitor, or not containing the buffering agent.

The following embodiments are contemplated:

Embodiment 1

An inclusion complex of meloxicam in a cyclodextrin.

Embodiment 2

A dosage form comprising: 1) the inclusion complex of embodiment 1, or 2) meloxicam and a carbonate or a bicarbonate.

Embodiment 3

The dosage form of embodiment 2 comprising the inclusion complex, wherein the cyclodextrin comprises substituted β-cyclodextrin.

Embodiment 4

The dosage form of embodiment 3, wherein the substituted β-cyclodextrin is a sulfobutyl ether β-cyclodextrin (SBEβCD) or hydroxypropyl β-cyclodextrin (HPBCD).

Embodiment 5

The dosage form of embodiment 4, wherein the cyclodextrin is the SBEβCD.

Embodiment 6

The dosage form of embodiment 5, wherein the SBEβCD has about 6 to about 7 sulfobutyl ether groups for each molecule of β-cyclodextrin.

Embodiment 7

The dosage form of embodiment 6, wherein the meloxicam and the SBEβCD have a molar ratio of about 0.8 to about 1.2.

Embodiment 8

The dosage form of embodiment 6, wherein the meloxicam and the SBEβCD have a molar ratio of about 1.

Embodiment 9

The dosage form of embodiment 2, 3, 4, 5, 6, 7, or 8, comprising a bicarbonate.

Embodiment 10

The dosage form of embodiment 9, wherein the bicarbonate comprises sodium bicarbonate.

Embodiment 11

The dosage form of embodiment 2, 3, 4, 5, 6, 7, 8, 9, or 10, which is an oral dosage form.

Embodiment 12

The dosage form of embodiment 2, 3, 4, 5, 6, 9, 10, or 11, wherein about 50 mg to about 200 mg of SBEβCD is present in the dosage form.

Embodiment 13

The dosage form of embodiment 2, 3, 4, 5, 6, 7, 8, 9, 10, 11, or 12, wherein the carbonate or bicarbonate is present in an amount in a range of about 400 mg to about 600 mg.

Embodiment 14

The dosage form of embodiment 2, 3, 4, 5, 6, 7, 8, 9, 10, 11, 12, or 13, wherein the $T_{max}$ of meloxicam is decreased as compared to a dosage form not having a carbonate, a bicarbonate, or a cyclodextrin.

Embodiment 15

The method of embodiment 14, wherein the $T_{max}$ of meloxicam is achieved in the patient at a time in a range of about 10 minutes to about 180 minutes after administration.

Embodiment 16

The dosage form of embodiment 2, 3, 4, 5, 6, 7, 8, 9, 10, 11, 12, 13, 14, or 15, having an oral bioavailability of meloxicam that is higher than a dosage form not having a carbonate, a bicarbonate, or a cyclodextrin.

Embodiment 17

The dosage form of embodiment 2, 3, 4, 5, 6, 7, 8, 9, 10, 11, 12, 13, 14, 15, or 16, further comprising an acid inhibitor.

Embodiment 18

The dosage form of embodiment 17, wherein the acid inhibitor is a proton pump inhibitor.

Embodiment 19

The dosage form of embodiment 18, wherein the proton pump inhibitor is esomeprazole.

Embodiment 20

The dosage form of embodiment 19, wherein about 30 mg to about 50 mg of esomeprazole is present in the dosage form.

Embodiment 21

A method of administering meloxicam orally, comprising orally administering a dosage form of embodiment 2, 3, 4, 5, 6, 7, 8, 9, 10, 11, 12, 13, 14, 15, 16, 17, 18, 19, or 20 to a patient in need of treatment.

Embodiment 22

The method of embodiment 21, wherein the dosage form is administered to treat pain.

Embodiment 23

The method of embodiment 21, wherein the dosage form is administered to treat inflammatory pain.

Embodiment 24

The method of embodiment 21, wherein the dosage form is administered to treat osteoarthritis, rheumatoid arthritis, or juvenile rheumatoid arthritis.

Embodiment 25

A method of administering meloxicam intravenously, comprising intravenously administering a dosage form of embodiment 2, 3, 4, 5, 6, 7, 8, 9, 10, 12, 13, 14, or 15, to a patient in need of treatment.

Embodiment 26

An inclusion complex of frovatriptan in a cyclodextrin.

Embodiment 2-1

A dosage form comprising: 1) the inclusion complex of frovatriptan in a cyclodextrin, or 2) frovatriptan and a carbonate or a bicarbonate.

Embodiment 2-2

The dosage form of Embodiment 2-1, comprising the inclusion complex, wherein the cyclodextrin comprises a sulfobutyl ether β-cyclodextrin (SBEβCD) or a hydroxypropyl β-cyclodextrin (HPβCD).

Embodiment 2-3

The dosage form of Embodiment 2-2, wherein the cyclodextrin is the SBEβCD and has about 6 to about 7 sulfobutyl ether groups for each molecule of β-cyclodextrin.

Embodiment 2-4

The dosage form of Embodiment 2-3, further comprising a bicarbonate.

Embodiment 2-5

The dosage form of Embodiment 2-4, wherein the bicarbonate comprises sodium bicarbonate.

Embodiment 2-6

The dosage form of Embodiment 2-3, wherein the frovatriptan and the SBEβCD have a molar ratio of about 0.8 to about 1.2.

Embodiment 2-7

The dosage form of Embodiment 2-6, further comprising a bicarbonate.

Embodiment 2-8

The dosage form of Embodiment 2-7, wherein the bicarbonate comprises sodium bicarbonate.

Embodiment 2-9

The dosage form of Embodiment 2-1, which is an oral dosage form.

Embodiment 2-10

The dosage form of Embodiment 2-2, comprising the inclusion complex, wherein about 50 mg to about 200 mg of the SBEβCD is present in a unit dosage form.

Embodiment 2-11

The dosage form of Embodiment 2-1, comprising frovatriptan and the carbonate or the bicarbonate.

Embodiment 2-12

The dosage form of Embodiment 2-1, wherein the $T_{max}$ of frovatriptan is decreased as compared to a dosage form without a carbonate, a bicarbonate, or a cyclodextrin.

Embodiment 2-13

The method of Embodiment 2-1, wherein the $T_{max}$ of frovatriptan is achieved in the patient at a time in a range of about 10 minutes to about 180 minutes after administration.

Embodiment 2-14

The dosage form of Embodiment 2-1, having an oral bioavailability of frovatriptan that is higher than a dosage form without a carbonate, a bicarbonate, or a cyclodextrin.

Embodiment 2-15

The dosage form of Embodiment 2-11, wherein the carbonate or the bicarbonate is present in a unit dosage form at an amount in a range of about 400 mg to about 600 mg.

Embodiment 2-16

The dosage form of Embodiment 2-15, wherein the carbonate or the bicarbonate is sodium bicarbonate.

Embodiment 2-17

The dosage form of Embodiment 2-11, further comprising an NSAID.

Embodiment 2-18

The dosage form of Embodiment 2-17, wherein the NSAID is a dexketoprofen or meloxicam.

Embodiment 2-19

The dosage form of Embodiment 2-18, wherein the NSAID is dexketoprofen.

Embodiment 2-20

The dosage form of Embodiment 2-19, wherein about 10 mg to about 50 mg of dexketoprofen is present in a unit dosage form.

Embodiment 2-21

A method of administering frovatriptan orally, comprising orally administering the dosage form of Embodiment 2-1 to a patient in need of treatment.

Embodiment 2-22

The method of Embodiment 2-21, wherein the dosage form comprises the inclusion complex, wherein the cyclodextrin is SBEβCD, and further comprises a bicarbonate.

Embodiment 2-23

The method of Embodiment 2-22, wherein the bicarbonate is sodium bicarbonate.

Embodiment 2-24

The method of Embodiment 2-23, wherein a unit dosage form contains about 300 mg to about 600 mg of sodium bicarbonate.

Embodiment 2-25

The method of Embodiment 2-22, wherein the dosage form further comprises a NSAID.

Embodiment 2-26

The method of Embodiment 2-25, wherein the NSAID is dexketoprofen, meloxicam, naproxen, ibuprofen, or celecoxib.

Embodiment 2-27

The method of Embodiment 2-21, wherein the dosage form is administered to treat pain.

Embodiment 2-28

The method of Embodiment 2-21, wherein the dosage form is administered to treat inflammatory pain.

Embodiment 2-29

The method of Embodiment 2-21, wherein the dosage form is administered to treat osteoarthritis, rheumatoid arthritis, or juvenile rheumatoid arthritis.

Embodiment P-1

A dosage form comprising:
meloxicam;
a sulfobutyl ether β-cyclodextrin (SBEβCD);
a bicarbonate; and
a triptan
wherein the dosage form is an oral dosage form having a shorter $T_{max}$ of meloxicam than a reference dosage form that: 1) contains the same amount of meloxicam, 2) does not contain an SBEβCD, and 3) does not contain a bicarbonate.

Embodiment P-2

The dosage form of Embodiment P-1, comprising an inclusion complex of 1) the meloxicam or the triptan and 2) the SBEβCD.

Embodiment P-3

The dosage form of Embodiment P-1 or P-2, containing about 10 mg to about 20 mg of meloxicam.

Embodiment P-4

The dosage form of Embodiment P-3, containing about 15 mg of meloxicam.

Embodiment P-5

The dosage form of Embodiment P-1, P-2, P-3, or P-4, wherein the SBEβCD has about 6 to about 7 sulfobutyl ether groups for each molecule of β-cyclodextrin.

Embodiment P-6

The dosage form of Embodiment P-1, P-2, P-3, P-4, or P-5, containing about 50 mg to about 200 mg of the SBEβCD.

Embodiment P-7

The dosage form of Embodiment P-1, P-2, P-3, P-4, P-5, or P-6, wherein the triptan is rizatriptan.

Embodiment P-8

The dosage form of Embodiment P-7, containing about 5 mg to about 20 mg of rizatriptan.

Embodiment P-9

The dosage form of Embodiment P-8, containing about 10 mg of rizatriptan.

Embodiment P-10

The dosage form of Embodiment P-6, containing about 100 mg of SBEβCD.

Embodiment P-11

The dosage form of Embodiment P-1, P-2, P-3, P-4, P-5, P-6, P-7, P-8, P-9, or P-10, wherein the bicarbonate comprises sodium bicarbonate.

Embodiment P-12

The dosage form of Embodiment P-10, containing about 400 mg to about 600 mg of the bicarbonate.

Embodiment P-13

The dosage form of Embodiment P-12, containing about 500 mg of sodium bicarbonate.

Embodiment P-14

The dosage form of Embodiment P-1, P-2, P-3, P-4, P-5, P-6, P-7, P-8, P-9, P-10, P-11, or P-12, wherein the oral dosage form has been shown to have a mean $T_{max}$ of meloxicam that is less than about 3 hours.

Embodiment P-15

The dosage form of Embodiment P-14, wherein the oral dosage form has been shown to have a mean $T_{max}$ of meloxicam that is less than about 2 hours.

Embodiment P-16

The dosage form of Embodiment P-14, wherein the oral dosage form has been shown to have a mean $T_{max}$ of meloxicam that is less than about 1 hour.

Embodiment P-17

The dosage form of Embodiment P-1, P-2, P-3, P-4, P-5, P-6, P-7, P-8, P-9, P-10, P-11, P-12, P-13, P-14, P-15, or P-16, wherein the oral dosage form has increased bioavailability of meloxicam as compared to the reference dosage form when administered to a mammal.

Embodiment P-18

The dosage form of Embodiment P-1, P-2, P-3, P-4, P-5, P-6, P-7, P-8, P-9, P-10, P-11, P-12, P-13, P-14, P-15, P-16, or P-17, wherein the oral dosage form has improved pharmacokinetics of meloxicam as compared to the reference dosage form when administered to a mammal.

Embodiment P-19

The dosage form of Embodiment P-1, P-2, P-3, P-4, P-5, P-6, P-7, P-8, P-9, P-10, P-11, P-12, P-13, P-14, P-15, P-16, P-17, or P-18, wherein the oral dosage form has increased bioavailability of the triptan as compared to the reference dosage form when administered to a mammal.

Embodiment P-20

The dosage form of Embodiment P-1, P-2, P-3, P-4, P-5, P-6, P-7, P-8, P-9, P-10, P-11, P-12, P-13, P-14, P-15, P-16, P-17, P-18, or P-19, wherein the oral dosage form has improved pharmacokinetics of the triptan as compared to the reference dosage form when administered to a mammal.

Embodiment P-21

A method of improving the pharmacokinetics of a triptan or an NSAID, comprising orally administering a dosage form of Embodiment P-1, P-2, P-3, P-4, P-5, P-6, P-7, P-8, P-9, P-10, P-11, P-12, P-13, P-14, P-15, P-16, P-17, P-18, P-19, or P-20 to a mammal or human being in need of treatment with the triptan or the NSAID.

Embodiment P-22

The method of treating pain, comprising orally administering a dosage form of Embodiment P-1, P-2, P-3, P-4, P-5, P-6, P-7, P-8, P-9, P-10, P-11, P-12, P-13, P-14, P-15, P-16, P-17, P-18, P-19, or P-20 to a mammal or human being in need thereof.

Embodiment P-23

The method of Embodiment P-22, wherein the pain is migraine.

Embodiment P-24

The method of Embodiment P-22, wherein the pain is inflammatory pain.

Example 1

The effect of varying amounts of potassium carbonate ($K_2CO_3$) and sodium bicarbonate ($NaHCO_3$) on the pH of acidic media was tested. The acidic media was chosen to simulate gastric conditions. $K_2CO_3$ or $NaHCO_3$ was added to 50 mL of a 0.01 N HCl solution (pH 2). The pH of the solution was measured after addition of the $K_2CO_3$ or NaHCO3. Deionized water (240 mL) was then added to the mixture and pH was measured again. The results are shown in Tables 1-4.

TABLE 1

| Results with $K_2CO_3$ (0.01N HCl) | |
|---|---|
| $K_2CO_3$ (mg) | pH |
| 25 | 2.84 |
| 35 | 6.29 |
| 45 | 8.05 |
| 50 | 8.29 |
| 100 | 9.43 |
| 200 | 10.14 |
| 300 | 10.39 |
| 400 | 10.55 |
| 450 | 10.58 |

TABLE 2

Results with $K_2CO_3$ (0.01N HCl + Water)

| $K_2CO_3$ (mg) | pH |
|---|---|
| 200 | 10.27 |
| 300 | 10.46 |
| 400 | 10.57 |
| 450 | 10.63 |

TABLE 3

Results with $NaHCO_3$ (0.01N HCl)

| $NaHCO_3$ (mg) | pH |
|---|---|
| 200 | 5.28 |
| 300 | 5.90 |
| 400 | 6.44 |
| 450 | 6.86 |
| 500 | 8.23 |
| 750 | 8.30 |
| 1000 | 8.36 |

TABLE 4

Results with $NaHCO_3$ (0.01N HCl + Water)

| $NaHCO_3$ (mg) | pH |
|---|---|
| 200 | 5.41 |
| 300 | 5.89 |
| 400 | 6.11 |
| 450 | 6.46 |
| 500 | 8.33 |
| 750 | 8.54 |
| 1000 | 8.60 |

Example 2

Tablets containing meloxicam and combinations of cyclodextrin, $K_2CO_3$, or $NaHCO_3$ were manufactured and tested for dissolution. Tablets containing meloxicam alone (MOBIC®) were purchased and also tested for dissolution. The tested tablets are listed in Table 5. Meloxicam in the form of meloxicam/cyclodextrin inclusion complexes was used in the tablets containing meloxicam and cyclodextrin. The inclusion complexes were formed by mixing meloxicam and cyclodextrin in an aqueous pH-adjusted solution. The pH of the solution was adjusted using buffering agents. The resulting soluble meloxicam/cyclodextrin inclusion complexes were then spray dried. This spray-dried dispersion was used in the manufacture of the tablets containing cyclodextrin.

TABLE 5

Tablets

| Tablet A | 15 mg meloxicam + 25 mg $K_2CO3$ |
|---|---|
| Tablet B | 15 mg meloxicam + 50 mg $K_2CO3$ |
| Tablet C | 15 mg meloxicam + 100 mg $K_2CO3$ |
| Tablet D | 15 mg meloxicam + 150 mg $K_2CO3$ |
| Tablet E | 15 mg meloxicam + 500 mg NaHCO3 |
| Tablet F | 15 mg meloxicam + 100 mg SBEβCD |
| Tablet G | 15 mg meloxicam + 100 mg SBEβCD + 25 mg $K_2CO3$ |
| Tablet H | 15 mg meloxicam + 100 mg SBEβCD + 50 mg $K_2CO3$ |
| Tablet I | 15 mg meloxicam + 100 mg SBEβCD + 100 mg $K_2CO3$ |
| Tablet J | 15 mg meloxicam + 100 mg SBEβCD + 150 mg $K_2CO3$ |
| Tablet K | 15 mg meloxicam + 100 mg SBEβCD + 500 mg NaHCO3 |
| Tablet L | 15 mg meloxicam (MOBIC ®) |

Dissolution testing in acidic medium (chosen to simulate gastric conditions) was performed by placing the tablets in a 0.01 N HCl solution, at an agitation rate of 75 RPM, and vessel temperature of approximately 37° C. The results are presented in Tables 6 and in FIGS. 1-10. Results at various time points (0, 15, 30, 45, 60, 90, and 120 minutes) are presented as percent (%) of meloxicam dissolved.

TABLE 6

Dissolution Results

| | 0 mins | 15 mins | 30 mins | 45 mins | 60 mins | 90 mins | 120 mins |
|---|---|---|---|---|---|---|---|
| Tablet A | 0% | 23% | 17% | 15% | 13% | 12% | 11% |
| Tablet B | 0% | 27% | 20% | 17% | 16% | 17% | 15% |
| Tablet C | 0% | 31% | 26% | 25% | 24% | 23% | 21% |
| Tablet D | 0% | 30% | 26% | 25% | 24% | 23% | 22% |
| Tablet E | 0% | 50% | 66% | 77% | 84% | 92% | 95% |
| Tablet F | 0% | 26% | 17% | 14% | 12% | 11% | 10% |
| Tablet G | 0% | 48% | 39% | 26% | 20% | 16% | 14% |
| Tablet H | 0% | 44% | 30% | 22% | 17% | 16% | 13% |
| Tablet I | 0% | 32% | 33% | 27% | 21% | 16% | 15% |
| Tablet J | 0% | 26% | 27% | 19% | 15% | 12% | 11% |
| Tablet K | 0% | 85% | 86% | 86% | 86% | 86% | 86% |
| Tablet L | 0% | 2% | 2% | 2% | 2% | 2% | 2% |

Dissolution of meloxicam was greater with the tablets containing various combinations of meloxicam and cyclodextrin, $K_2CO_3$, or $NaHCO_3$, as compared to tablets containing meloxicam alone. For example, after 120 minutes, dissolution of meloxicam tablets containing $NaHCO_3$ was 95% as compared to 2% for tablets containing meloxicam alone.

Dissolution of meloxicam increases with increasing amounts of $K_2CO_3$ in the absence of cyclodextrin. However, in the presence of cyclodextrin, increasing amounts of $K_2CO_3$ did not appear to increase meloxicam dissolution. At the highest dose of potassium carbonate tested, meloxicam dissolution in the presence of cyclodextrin was reduced by approximately 50% as compared to meloxicam dissolution in the absence of cyclodextrin at 120 minutes.

Dissolution of meloxicam with $NaHCO_3$ was significantly greater than that observed with the highest dose of $K_2CO_3$ at 15 minutes (50% versus 30%), and at 120 minutes (92% versus 23%). Meloxicam dissolution in the presence of cyclodextrin was also significantly greater with $NaHCO_3$ as compared to the highest dose of $K_2CO_3$ at 15 minutes (85% versus 26%), and at 120 minutes (86% versus 12%). $NaHCO_3$ in the presence of cyclodextrin increased meloxicam dissolution at 15 minutes as compared to potassium bicarbonate which resulted in a reduction in dissolution.

Example 3

A bilayer tablet containing 1) an inclusion complex of SBEβCD with meloxicam, and 2) sodium bicarbonate that was prepared (SBEβCD-Meloxicam/Bicarbonate). The first layer contained an inclusion complex of 15 mg meloxicam and 100 mg SBEβCD, and 100 mg of sodium bicarbonate. The second layer contained 40 mg of esomeprazole and 400 mg of sodium bicarbonate.

A total of 20 human subjects were randomly assigned in a 1:1 ratio to treatment with the SBEβCD-Meloxicam/Bicarbonate tablets described above or Mobic® tablets (15 mg meloxicam), once daily for 6 days under fasting conditions.

Figure 11:
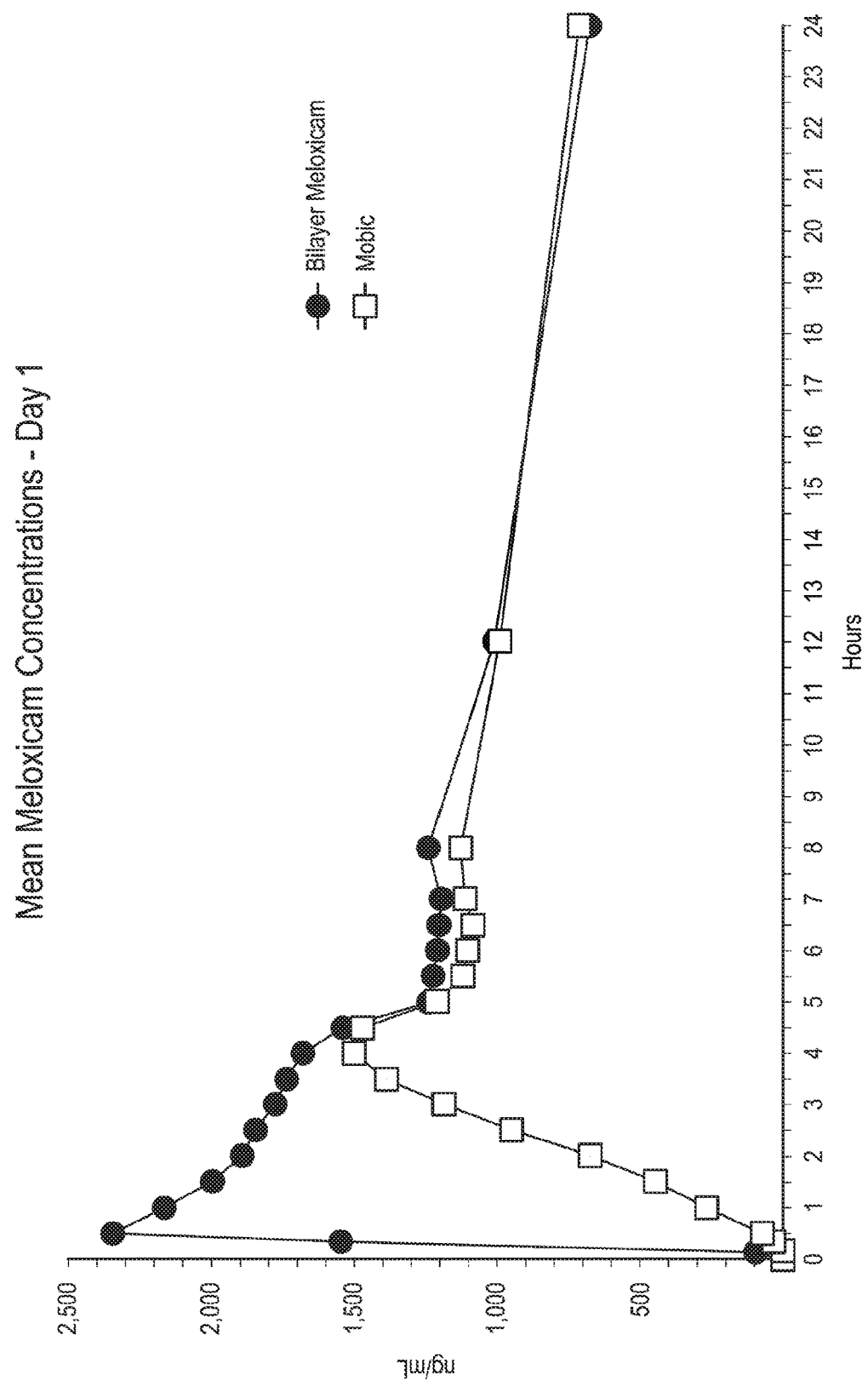
FIG. 11 is a plot of meloxicam plasma concentration at various time points over the first 24 hours for an embodiment of a dosage form described herein and a commercially available meloxicam dosage form.

On the first day of dosing, plasma samples were collected for concentration analysis of meloxicam at several time points. Concentrations of meloxicam were determined using LC-MS/MS. Pharmacokinetic parameters were calculated. The results are depicted in FIG. 11.

The median $T_{max}$ for meloxicam, the trial's primary endpoint, was 9 times faster for the SBEβCD-Meloxicam/Bicarbonate tablets as compared to Mobic® (0.5 hour versus 4.5 hours respectively, p<0.0001).

The SBEβCD-Meloxicam/Bicarbonate tablets also demonstrated higher mean maximum plasma concentration ($C_{max}$) (p=0.0018), faster time to therapeutic plasma concentration (p<0.0001), and faster time to half-maximal plasma concentration (p<0.0001) as compared to Mobic®.

Unless otherwise indicated, all numbers expressing quantities of ingredients, properties such as molecular weight, reaction conditions, and so forth used in the specification and claims are to be understood in all instances as indicating both the exact values as shown and as being modified by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

The invention claimed is:

1. A dosage form comprising a combination of: 1) a complex of meloxicam with a sulfobutyl ether β-cyclodextrin (SBEβCD), 2) a bicarbonate, and 3) a triptan; wherein the dosage form contains 400 mg to 600 mg of the bicarbonate, about 5 mg to about 50 mg of meloxicam, and about 50 mg to about 200 mg of SBEβCD; and wherein the dosage form is a solid oral dosage form having a shorter $T_{max}$ of meloxicam in a human being than a reference dosage form that: 1) contains the same amount of meloxicam, 2) does not contain an SBEβCD, and 3) does not contain a bicarbonate.

2. The dosage form of claim 1, wherein the triptan is a rizatriptan.

3. The dosage form of claim 2, wherein about 8 mg to about 13 mg of the rizatriptan is present in the dosage form based upon the weight of the rizatriptan in the free base form.

4. The dosage form of claim 3, wherein the rizatriptan is present in a salt form in an amount that is a molar equivalent of about 10 mg of the rizatriptan in the free base form.

5. The dosage form of claim 4, wherein the rizatriptan is present as rizatriptan benzoate.

6. The dosage form of claim 1, containing about 15 mg to about 25 mg of meloxicam.

7. The dosage form of claim 1, containing about 20 mg of meloxicam.

8. The dosage form of claim 1, wherein the SBEβCD has about 6 to about 7 sulfobutyl ether groups for each molecule of β-cyclodextrin.

9. The dosage form of claim 1, containing about 100 mg to about 175 mg of the SBEβCD.

10. The dosage form of claim 1, containing about 100 mg to about 140 mg of SBEβCD.

11. The dosage form of claim 1, wherein the bicarbonate comprises sodium bicarbonate.

12. The dosage form of claim 11, containing about 500 mg of sodium bicarbonate.

13. The dosage form of claim 1, wherein the oral dosage form has been shown to have a median $T_{max}$ of meloxicam that is less than about 3 hours in fasted human subjects.

14. The dosage form of claim 1, wherein the oral dosage form has been shown to have a median $T_{max}$ of meloxicam that is less than about 2 hours in fasted human subjects.

15. The dosage form of claim 1, wherein the oral dosage form has been shown to have a median $T_{max}$ of meloxicam that is less than about 1 hour in fasted human subjects.

16. The dosage form of claim 1, wherein the oral dosage form has been shown to have a median $C_{max}$ of meloxicam that is at least 1800 ng/mL in fasted human subjects.

17. The dosage form of claim 1, wherein the oral dosage form has been shown to have a median $AUC_{0-6}$ of meloxicam that is at least 6,000 ng·hr/mL in fasted human subjects.

18. The dosage form of claim 1, wherein the oral dosage form has been shown to have a median time to half-maximal plasma concentration of meloxicam that is less than about 30 minutes in fasted human subjects.

19. A method of treating migraine, comprising administering a dosage form of claim 1 to a human being in need thereof.

20. The method of claim 19, wherein the oral dosage form has been shown to have a median $T_{max}$ of meloxicam that is less than about 1 hour in fasted human subjects.

21. The method of claim 19, wherein the oral dosage form has been shown to have a median $C_{max}$ of meloxicam that is at least 1800 ng/mL in fasted human subjects.

22. The method of claim 19, wherein the oral dosage form has been shown to have a median $AUC_{0-6}$ of meloxicam that is at least 6,000 ng·hr/mL in fasted human subjects.

23. The method of claim 19, wherein the oral dosage form has been shown to have a median time to half-maximal plasma concentration of meloxicam that is less than about 30 minutes in fasted human subjects.

24. The method of claim 19, wherein the triptan is a rizatriptan.

25. The method of claim 24, wherein about 5 mg to about 20 mg of the rizatriptan is present in the dosage form based upon the weight of the rizatriptan in the free base form.

26. The method of claim 25, wherein the rizatriptan is present in a salt form in an amount that is a molar equivalent of about 10 mg of the rizatriptan in the free base form.

27. The method of claim 26, wherein the rizatriptan is present as rizatriptan benzoate.

28. The method of claim 19, wherein the dosage form contains about 10 mg to about 30 mg of meloxicam.

29. The method of claim 19, wherein the dosage form contains about 20 mg of meloxicam.

* * * * *

UNITED STATES PATENT AND TRADEMARK OFFICE
CERTIFICATE OF CORRECTION

PATENT NO. : 10,137,131 B2
APPLICATION NO. : 15/936176
DATED : November 27, 2018
INVENTOR(S) : Herriot Tabuteau It is certified that error appears in the above-identified patent and that said Letters Patent is hereby corrected as shown below:

In the Claims

Column 34, Line 44, Claim 12: Remove "about" before "500 mg"

Signed and Sealed this
Twenty-fifth Day of June, 2019

Andrei Iancu
*Director of the United States Patent and Trademark Office*